United States Patent
Fujita et al.

(10) Patent No.: US 12,029,386 B2
(45) Date of Patent: Jul. 9, 2024

(54) ENDOSCOPY SERVICE SUPPORT DEVICE, ENDOSCOPY SERVICE SUPPORT SYSTEM, AND METHOD OF OPERATING ENDOSCOPY SERVICE SUPPORT DEVICE

(71) Applicant: FUJIFILM Corporation, Tokyo (JP)

(72) Inventors: Hiroshi Fujita, Kanagawa (JP); Haruo Akiba, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 183 days.

(21) Appl. No.: 17/748,728

(22) Filed: May 19, 2022

(65) Prior Publication Data

US 2022/0378276 A1 Dec. 1, 2022

(30) Foreign Application Priority Data

May 26, 2021 (JP) ................................. 2021-088695

(51) Int. Cl.
| | | |
|---|---|---|
| *A61B 1/00* | (2006.01) | |
| *A61B 1/06* | (2006.01) | |
| *A61B 5/107* | (2006.01) | |
| *G02B 23/24* | (2006.01) | |

(52) U.S. Cl.
CPC ...... *A61B 1/00009* (2013.01); *A61B 1/00045* (2013.01); *A61B 1/00096* (2013.01); *A61B 1/0676* (2013.01); *A61B 5/1076* (2013.01); *A61B 5/1079* (2013.01); *G02B 23/24* (2013.01)

(58) Field of Classification Search
CPC ...... G02B 23/24; G06N 20/00; G06T 7/0012; G06T 7/62; G06T 7/90; G06T 2207/10024; G06T 2207/10068; G06T 2207/20081; G06T 2207/20084; G06T 2207/30096

See application file for complete search history.

(56) References Cited

U.S. PATENT DOCUMENTS

| | | | | |
|---|---|---|---|---|
| 7,684,599 B2 * | 3/2010 | Horn | ...................... | A61B 5/065 382/199 |
| 8,521,261 B2 * | 8/2013 | Okawa | ................... | A61B 1/043 600/478 |

(Continued)

FOREIGN PATENT DOCUMENTS

| | | |
|---|---|---|
| EP | 4016162 A1 | 6/2022 |
| JP | 2016-062488 A | 4/2016 |

(Continued)

OTHER PUBLICATIONS

The extended European search report issued by the European Patent Office on Oct. 11, 2022, which corresponds to European Patent Application No. 22175475.7-1126 and is related to U.S. Appl. No. 17/748,728.

*Primary Examiner* — Sath V Perungavoor
*Assistant Examiner* — Paramita Ghosh
(74) *Attorney, Agent, or Firm* — Studebaker & Brackett PC

(57) ABSTRACT

An image reception unit receives a still image acquired by an endoscope system. The still image combination unit performs still image collation processing for collating an internal still image and an external still image out of the still images, combines the internal still image with the external still image on the basis of at least a result of the still image collation processing, and displays the combined internal still image and external still image on a service support display.

12 Claims, 24 Drawing Sheets

(56) References Cited

U.S. PATENT DOCUMENTS

| | | | |
|---|---|---|---|
| 2008/0108873 A1* | 5/2008 | Gattani | A61B 1/045 |
| | | | 382/128 |
| 2012/0307039 A1* | 12/2012 | Holmes | H04N 7/183 |
| | | | 348/82 |
| 2013/0002844 A1* | 1/2013 | Shida | A61B 1/000094 |
| | | | 348/E7.085 |
| 2013/0116508 A1 | 5/2013 | Shida | |
| 2013/0286174 A1 | 10/2013 | Urakabe | |
| 2016/0287141 A1 | 10/2016 | Sidlesky | |
| 2018/0308247 A1* | 10/2018 | Gupta | G06T 7/62 |
| 2020/0107698 A1* | 4/2020 | Tatsuta | A61B 1/0623 |
| 2020/0410721 A1* | 12/2020 | Farri | G16H 50/20 |

FOREIGN PATENT DOCUMENTS

| | | |
|---|---|---|
| JP | 2016-198304 A | 12/2016 |
| JP | 2017-508529 A | 3/2017 |
| JP | 2017-217215 A | 12/2017 |
| WO | 2021/029277 A1 | 2/2021 |

\* cited by examiner

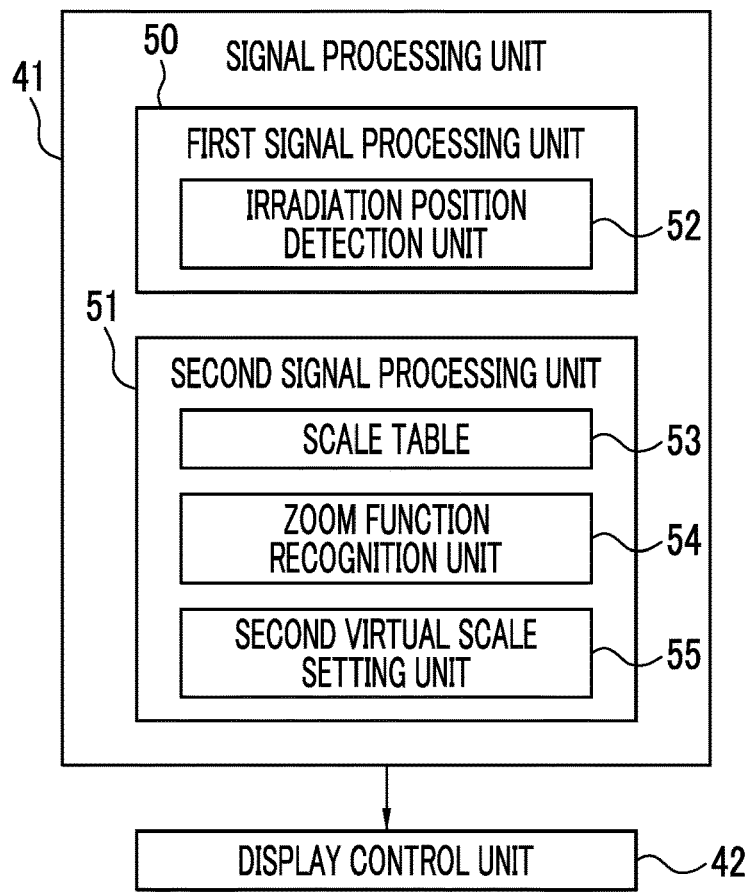

FIG. 10
| CROSS SHAPE | GRADUATED CROSS SHAPE | DISTORTED CROSS SHAPE | CIRCLE AND CROSS SHAPE | MEASUREMENT POINT GROUP SHAPE |
|---|---|---|---|---|
| 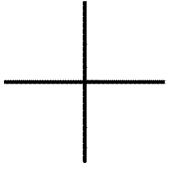 | 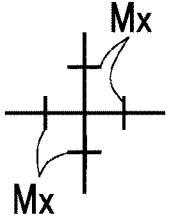 Mx Mx | 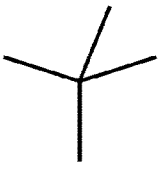 | 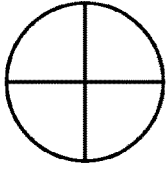 | 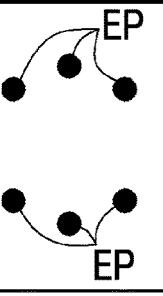 EP EP |
FIG. 11
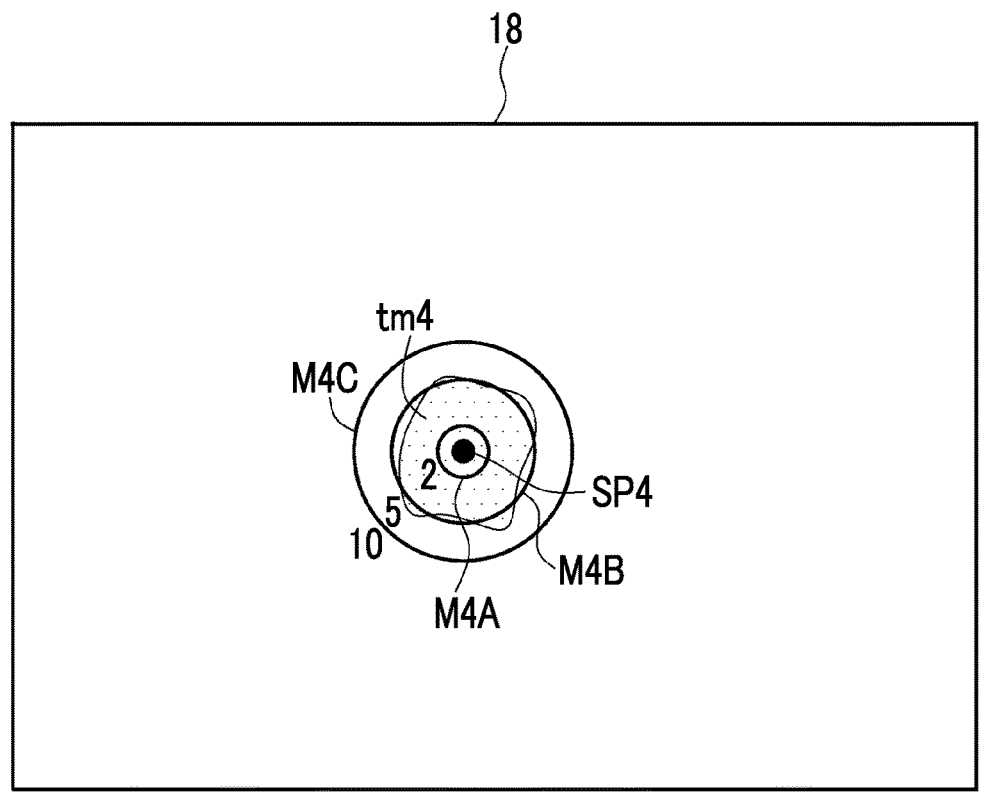

ENDOSCOPY SERVICE SUPPORT DEVICE, ENDOSCOPY SERVICE SUPPORT SYSTEM, AND METHOD OF OPERATING ENDOSCOPY SERVICE SUPPORT DEVICE

CROSS-REFERENCE TO RELATED APPLICATIONS

This application claims priority under 35 U.S.C. § 119(a) to Japanese Patent Application No. 2021-088695 filed on 26 May 2021. The above application is hereby expressly incorporated by reference, in its entirety, into the present application.

BACKGROUND OF THE INVENTION

1. Field of the Invention

The present invention relates to an endoscopy service support device, an endoscopy service support system, and a method of operating the endoscopy service support device, which support the creation of medical documents.

2. Description of the Related Art

In the medical field using endoscopes, in addition to observing the inside of a patient's body, a procedure for removing a lesion or the like by using various treatment tools is also performed (refer to, for example, JP2016-62488A). In a case where the lesion is removed, endoscopy service such as creating medical documents such as an endoscope report is performed using a still image of the inside of the body in the removed range and a still image of the removed specimen.

SUMMARY OF THE INVENTION

In a case where a procedure such as removal of a lesion is performed, a still image is acquired by the same operation or processing even during treatment using an endoscope or at the time of imaging a specimen after the treatment. For that reason, since still images are saved without the distinction between the inside of the body or the outside the body, it is necessary for a user to manually select the still images necessary for creating reports, or the like at the stage of creating medical documents, which is burdensome.

An object of the present invention is to provide an endoscopy service support device, an endoscopy service support system, and a method of operating an endoscopy service support device capable of selecting and displaying an internal still image and an external still image without imposing a burden on a user.

An endoscopy service support device of the present invention comprises a processor for service support. The processor for service support receives a still image acquired by an endoscope system, performs still image collation processing for collating an internal still image and an external still image out of the still images, combines the internal still image with the external still image on the basis of at least a result of the still image collation processing, and displays the combined internal still image and external still image on a service support display.

It is preferable that the processor for service support discriminates whether the still image is the internal still image or the external still image. It is preferable that the internal still image or the external still image is associated with an examination purpose including treatment or observation, and the processor for service support combines the external still image with an internal still image of which the examination purpose is the treatment, out of the internal still images that match the external still image as a result of the still image collation processing. It is preferable that length measurement information is associated with the internal still image or the external still image, and the processor for service support combines the external still image with an internal still image of which the length measurement information matches that of the external still image, out of the internal still images that match the external still image, as a result of the still image collation processing.

It is preferable that the service support display is provided with a length measurement information display region for displaying length measurement information of at least one of the internal still image or the external still image, and an examination purpose selection screen for selecting an examination purpose.

An endoscopy service support system of the present invention comprises an endoscope system having an endoscope that acquires a still image manually or automatically obtained by imaging a subject by using an imaging optical system, and the endoscopy service support device described above. The internal still image or the external still image is obtained by the endoscope.

It is preferable that the endoscope has a measurement light emitting unit that emits a measurement light in a state where an optical axis of the measurement light and an optical axis of the imaging optical system intersect each other, and acquires the still image by imaging the subject illuminated with the measurement light by using the imaging optical system, and the endoscope system includes processor device that acquires length measurement information on the basis of an irradiation position of the measurement light included in the still image.

It is preferable that the length measurement information is information based on a virtual scale for measuring a size of the subject, the processor device includes an endoscope processor, and the endoscope processor is configured to detect an irradiation position of the measurement light from the still image, and set a first virtual scale in which a scale display position varies in accordance with the irradiation position of the measurement light as the virtual scale by referring to a scale table in which a virtual scale image of which a display mode varies depending on the irradiation position of the measurement light and the scale display position and the irradiation position of the measurement light are stored in association with each other.

It is preferable that the length measurement information is information based on a virtual scale for measuring the size of the subject, the endoscope has a zoom function, the processor device includes an endoscope processor, and the endoscope processor is configured to set a second virtual scale of which a scale display position is fixed as the virtual scale in a case where the zoom function is ON and has a magnification ratio equal to or more than a specific magnification ratio. It is preferable that the second virtual scale has the same display mode regardless of a position of a screen, or has a display mode that varies depending on the position of the screen.

In a method of operating the endoscopy service support device of the present invention, the method is executed by a processor for service support and includes a step of receiving a still image acquired by an endoscope system; a step of performing still image collation processing for collating an internal still image with an external still image out of the still images and combining the internal still image with the external still image on the basis of at least a result of the still image collation processing, and a step of displaying the combined internal still image and external still image on a service support display.

According to the present invention, it is possible to select and display the internal still image and the external still image without imposing a burden on a user.

BRIEF DESCRIPTION OF THE DRAWINGS

FIG. 4A is an explanatory diagram showing light emission control in a case where the measurement light is continuously emitted, and FIG. 4B is an explanatory diagram showing light emission control in a case where the measurement light is pulse-emitted.

FIG. 5 is a block diagram showing functions of a signal processing unit.

FIG. 10 is an explanatory diagram showing the first virtual scales having various shapes.

FIG. 11 is an explanatory diagram showing the first virtual scales having different sizes.

DESCRIPTION OF THE PREFERRED EMBODIMENTS

Figure 1:
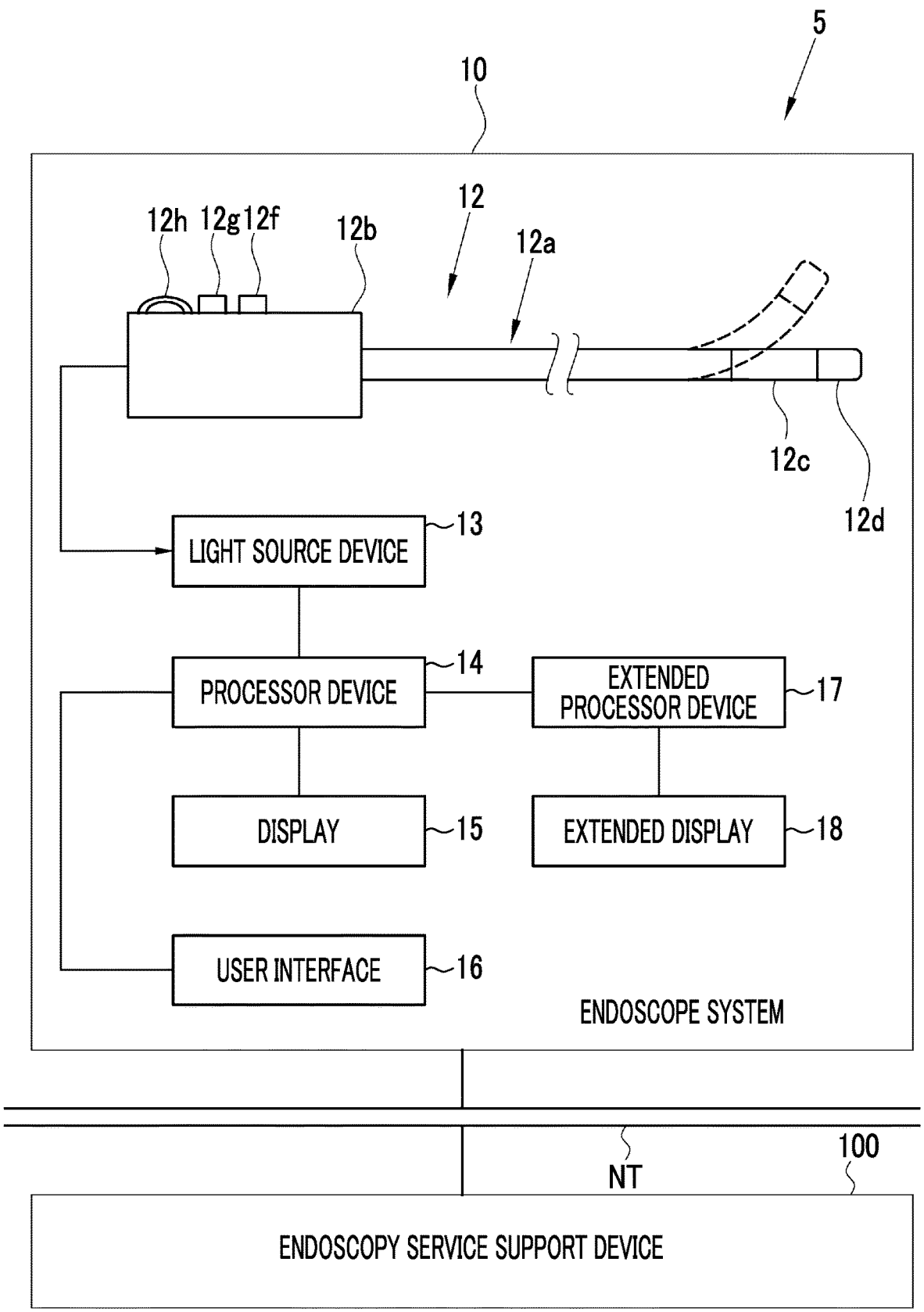
FIG. 1 is a schematic diagram of an endoscopy service support system showing respective functions of an endoscope system.

As shown in FIG. 1, an endoscopy service support system 5 comprises an endoscope system 10 for observing or treating the inside of a patient's body, and an endoscopy service support device 100 that supports the creation of medical documents such as endoscope reports by an image obtained by the endoscope system 10. The endoscope system 10 and the endoscopy service support device 100 can communicate various data such as images via a network NT.

The endoscope system 10 includes an endoscope 12, a light source device 13, a processor device 14, a display 15, a user interface 16, an extended processor device 17, and an extended display 18. The endoscope 12 is optically connected to the light source device 13 and electrically connected to the processor device 14. The endoscope 12 has an insertion part 12a to be inserted into the inside of a body, which is an object to be observed, an operating part 12b provided at a proximal end portion of the insertion part 12a, and a bendable part 12c and a distal end part 12d provided on a distal end side of the insertion part 12a. The bendable part 12c is operated in a bendable manner by operating the operating part 12b. The distal end part 12d is directed in a desired direction by the bending operation of the bendable part 12c.

Additionally, the operating part 12b is provided with a mode selection switch 12f used for the operation of switching an observation mode, a still image acquisition instruction switch 12g used for giving an instruction on the acquisition of a still image of the object to be observed, and a zoom operation part 12h used for operating a zoom lens 21b.

The processor device 14 is electrically connected to the display 15 and the user interface 16. The display 15 outputs and displays an image, information, or the like of the object to be observed, which has been processed by the processor device 14. The user interface 16 has a keyboard, a mouse, a touch pad, a microphone, and the like and has a function of receiving input operations such as function settings. The extended processor device 17 is electrically connected to the processor device 14. The extended display 18 outputs and displays an image, information, or the like processed by the extended processor device 17.

The endoscope 12 comprises a normal observation mode, a special light observation mode, and a length measurement mode and is switched by the mode selection switch 12f. The normal observation mode is a mode in which the object to be observed is illuminated with illumination light. The special light observation mode is a mode in which the object to be observed is illuminated with special light different from the illumination light. In the length measurement mode, the object to be observed is illuminated with the illumination light or the measurement light, and a virtual scale used for measuring the size or the like of the object to be observed is displayed on a subject image obtained by imaging the object to be observed. The subject image on which the virtual scale is not superimposed is displayed on the display 15, while the subject image on which the virtual scale is superimposed is displayed on the extended display 18.

In addition, the illumination light is the light used for observing the entire object to be observed by giving brightness to the entire object to be observed. The special light is the light used to enhance a specific region of the object to be observed. The measurement light is the light used for displaying the virtual scale. Additionally, in the present embodiment, the virtual scale displayed on the image will be described, but an actual scale may be provided in an actual lumen such that the actual scale can be checked through the image. In this case, it is conceivable that the actual scales are inserted through a forceps channel of the endoscope 12 and the actual scales are made to protrude from the distal end part 12d.

As a user operates the still image acquisition instruction switch 12g, a screen of the display 15 is freeze-displayed and also emits an alert sound (for example, "beep") to the effect that the still image is acquired. Then, the still image of the subject image obtained before and after the operation timing of the still image acquisition instruction switch 12g is stored in a still image saving unit 37 (refer to FIG. 2) in the processor device 14. In addition, the still image saving unit 37 is a storage unit such as a hard disk or a USB (Universal Serial Bus) memory. In a case where the processor device 14 can be connected to the network, the still image of the subject image may be saved in a still image saving server (not shown) connected to the network instead of or in addition to the still image saving unit 37.

In addition, a still image acquisition instruction may be given by using an operation device other than the still image acquisition instruction switch 12g. For example, a foot pedal may be connected to the processor device 14, and in a case where the user operates the foot pedal (not shown) with his/her foot, the still image acquisition instruction may be given. Mode switching may be performed with the foot pedal. Additionally, a gesture recognition unit (not shown) that recognizes a user's gesture may be is connected to the processor device 14, and in a case where the gesture recognition unit recognizes a specific gesture performed by the user, the still image acquisition instruction may be given. The mode switching may also be performed using the gesture recognition unit.

Additionally, a visual line input unit (not shown) provided near the display 15 may be connected to the processor device 14, and in a case where the visual line input unit recognizes that the user's line of sight is within a predetermined region of the display 15 for a certain period of time or longer, the still image acquisition instruction may be given. Additionally, a voice recognition unit (not shown) may be connected to the processor device 14, and in a case where the voice recognition unit recognizes a specific voice emitted by the user, the still image acquisition instruction may be given. The mode switching may also be performed using the voice recognition unit. Additionally, an operation panel (not shown) such as a touch panel may be connected to the processor device 14, and in a case where the user performs a specific operation on the operation panel, the still image acquisition instruction may be given. The mode switching may also be performed using the operation panel.

Figure 2:
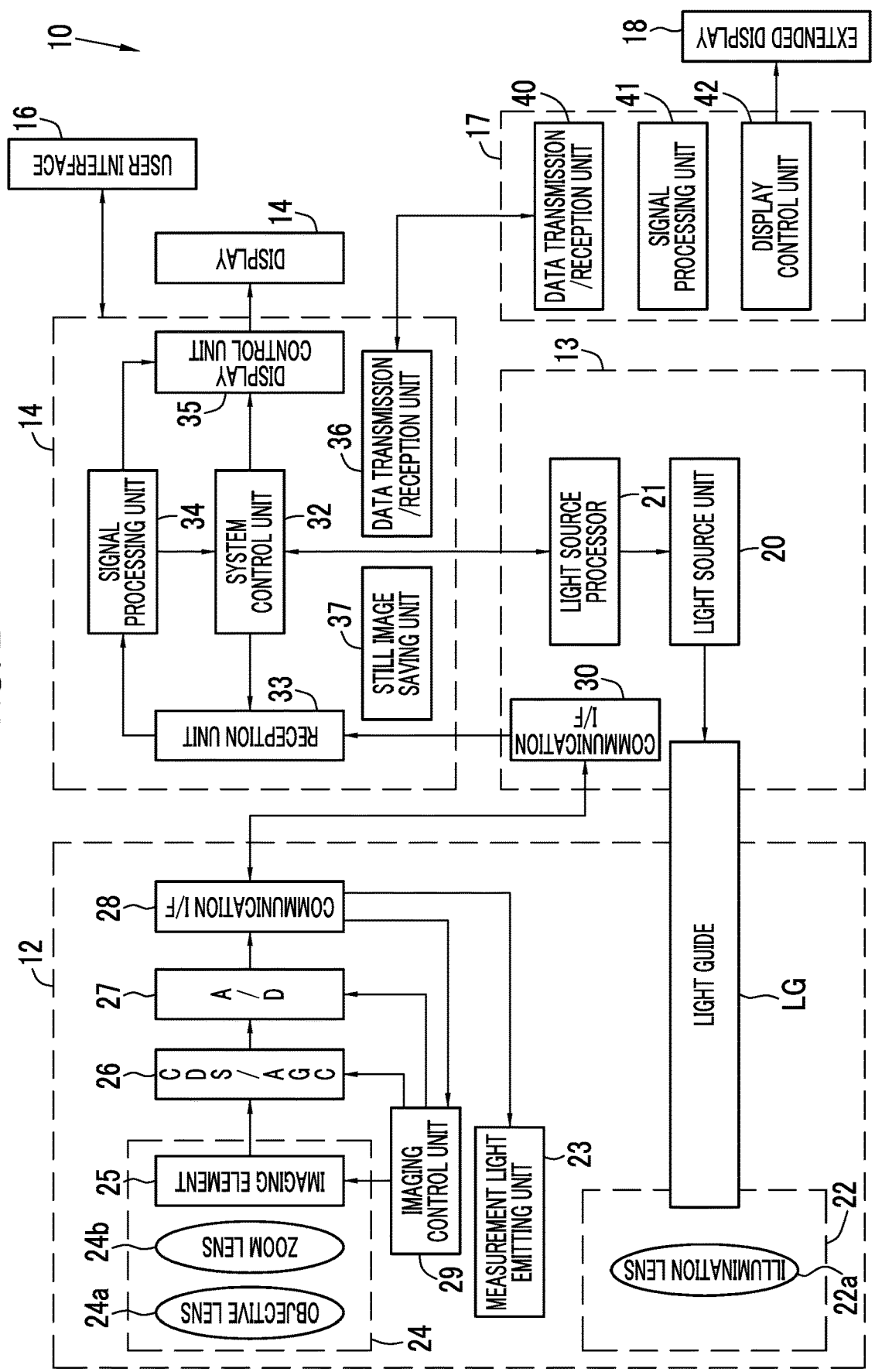
FIG. 2 is a block diagram showing the functions of an endoscope system.

As shown in FIG. 2, the light source device 13 comprises a light source unit 20 and a light source processor 21. The light source unit 20 generates the illumination light or special light for illuminating the subject. The illumination light or special light emitted from the light source unit 20 is incident on a light guide LG. The light from the light guide LG passes through an illumination lens 22a constituting an illumination optical system 22 and irradiates the subject. As the light source unit 20, a white light source that emits white light, or a plurality of light sources including the white light source and a light source (for example, a blue light source that emits blue light) that emits other color light, are used as light sources for the illumination light. Additionally, as the light source unit 20, a light source that emits wideband light including blue narrow band light for enhancing skin layer information such as skin layer blood vessels is used as a light source for the special light. In addition, the illumination light may be white mixed light that is a combination of at least one of purple light, blue light, green light, or red light. In this case, it is preferable to design the illumination optical system 22 such that the irradiation range of the green light is larger than the irradiation range of the red light.

The light source processor 21 controls the light source unit 20 on the basis of an instruction from the system control unit 32. In the case of the normal observation mode, the system control unit 32 controls to turn on the illumination light and turn off the measurement light. In the case of the special light observation mode, the system control unit 32 controls to turn on the special light and turn off the measurement light. In the case of the length measurement mode, the system control unit 32 controls to turn on or off the illumination light or the measurement light and also controls a measurement light emitting unit 23.

The imaging optical system 24 includes an objective lens 24a, a zoom lens 24b, and an imaging element 25. The reflected light from the object to be observed is incident on the imaging element 25 via the objective lens 24a and the zoom lens 24b. Accordingly, a reflected image of the object to be observed is formed on the imaging element 25. The zoom lens 24b has an optical zoom function for enlarging or reducing the subject as a zoom function by moving between a telephoto end and a wide end. The optical zoom function can be switched on and off by the zoom operation part 12h (refer to FIG. 1) provided in the operating part 12b of the endoscope, and the subject is enlarged or reduced in a specific magnification ratio by further operating the zoom operation part 12h in a state where the optical zoom function is ON.

The imaging element 25 is a color imaging sensor, which captures the reflected image of the subject to output an image signal. The imaging element 25 is controlled by the imaging control unit 29. The imaging element 25 is preferably a charge coupled device (CCD) imaging sensor, a complementary metal-oxide semiconductor (CMOS) imaging sensor, or the like. The imaging element 25 used in the present invention is a color imaging sensor for obtaining a red image, a green image, and a blue image in three colors of red (R), green (G), and blue (B). The red image is an image output from a red pixel provided with a red color filter in the imaging element 25. The green image is an image output from a green pixel provided with a green color filter in the imaging element 25. The blue image is an image output from a blue pixel provided with a blue color filter in the imaging element 25. The imaging element 25 is controlled by the imaging control unit 29.

The image signal output from the imaging element 25 is transmitted to a CDS/AGC circuit 26. The CDS/AGC circuit 26 performs correlated double sampling (CDS) and auto gain control (AGC)) on the image signal that is an analog signal. The image signal that has passed through the CDS/AGC circuit 26 is converted into a digital image signal by an analog/digital (A/D) converter 27. The A/D converted digital image signal is input to a communication interface (I/F) 30 of the light source device 13 via a communication interface (I/F) 28. In addition, a CDS/AGC circuit 26 and an A/D converter 27 are controlled by the imaging control unit 29.

In the processor device 14, a program related to various kinds of processing or control is incorporated in a program storage memory (not shown). The system control unit 32 constituted by an image control processor operates the program incorporated in the program storage memory, thereby realizing the functions of a reception unit 33, a signal processing unit 34, a display control unit 35, and a data transmission/reception unit 36, which are connected to the communication interface (I/F) 30 of the light source device 13.

The reception unit 33 receives an image signal transmitted from the communication I/F 30 to transmit the image signal to the signal processing unit 34. The signal processing unit 34 has a built-in memory for temporarily storing the image signal received from the reception unit 33, and processes an image signal group, which is a set of image signals stored in the memory, to generate the subject image. In addition, the reception unit 33 may directly send a control signal related to the light source processor 31 to the system control unit 32.

In the signal processing unit 34, in a case where the normal observation mode is set, a color subject image is displayed on the display 15 by performing signal allocation processing in which the blue image of the subject image is allocated on a B channel of the display 15, the green image of the subject image is allocated to a G channel of the display 15, and the red image of the subject image is allocated to an R channel of the display 15. Even in the length measurement mode, the same signal allocation processing as in the normal observation mode is performed.

Meanwhile, in the signal processing unit 34, in a case where the special light observation mode is set, a pseudo-color subject image is displayed on the display 15 by not using the red image of the subject image for the display of the display 15 but allocating the blue image of the subject image to the B channel and G channel of the display 15 and allocating the green image of the subject image to the R channel of the display 15. Additionally, the signal processing unit 34 transmits a subject image including an irradiation position of the measurement light to the data transmission/reception unit 36 in a case where the length measurement mode is set.

The data transmission/reception unit 36 transmits data related to the subject image to the extended processor device 17. In addition, the data transmission/reception unit 36 can receive the data or the like from the extended processor device 17. The received data can be processed by the signal processing unit 34 or the system control unit 32.

The display control unit 35 displays the subject image generated by the signal processing unit 34 on the display 15. The system control unit 32 performs various kinds of control on the endoscope 12, the light source device 13, the processor device 14, and the extended processor device 17. The imaging element 25 is controlled via the imaging control unit 29 provided in the endoscope 12.

The extended processor device 17 receives the data transmitted from the processor device 14 by the data transmission/reception unit 40. The signal processing unit 41 performs processing related to the length measurement mode on the basis of the data received by the data transmission/reception unit 40. Specifically, the processing of determining the size of the virtual scale from the subject image including the irradiation position of the measurement light and superimposing and displaying the determined virtual scale on the subject image is performed. The display control unit 42 displays the subject image on which the virtual scale is superimposed and displayed on the extended display 18. In addition, the data transmission/reception unit 40 can transmit the data or the like to the processor device 14.

Figure 3:
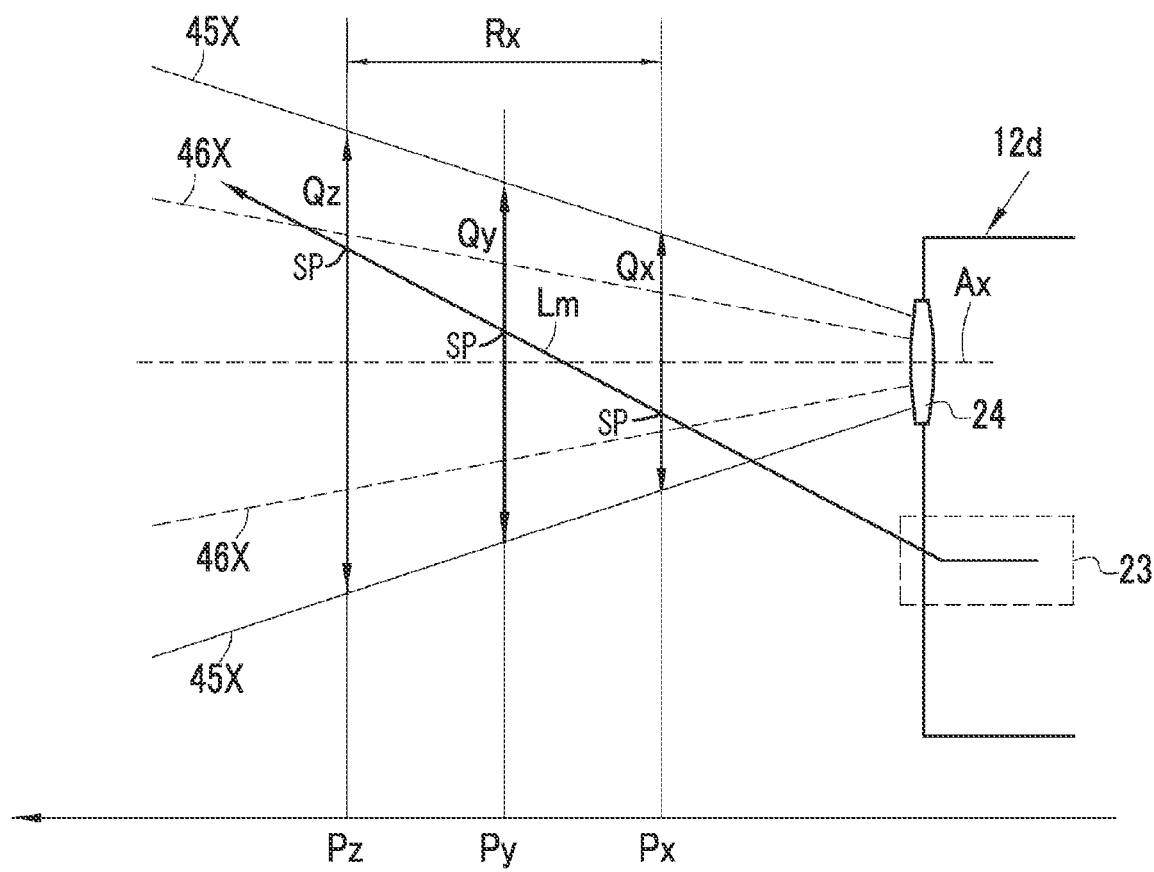
FIG. 3 is a schematic diagram showing a relationship between an optical axis of measurement light and an optical axis of an imaging optical system.

As shown in FIG. 3, the measurement light emitting unit 23 emits the measurement light in a state where an optical axis of the measurement light Lm intersects an optical axis Ax of the imaging optical system 24. Assuming that observation is possible in a range Rx of an observation distance, it can be seen that, in a near end Px, a center vicinity Py, and a far end Pz of the range Rx, the position (points where each of arrows Qx, Qy, and Qz intersect the optical axis of the measurement light Lm) of a spot SP formed on the subject by the measurement light Lm in an imaging range (indicated by each of the arrows Qx, Qy, and Qz) at each point are different from each other. In addition, the imaging angle of view of the imaging optical system 24 is represented by the inside of a region sandwiched between two solid lines 45X, and the measurement is performed in a central region (a region sandwiched between two dotted lines 46X) having less aberration in the imaging angle of view.

As described above, by emitting the measurement light Lm in a state where the optical axis of the measurement light Lm intersects the optical axis Ax, the size of the subject can be measured from the movement of a spot position with respect to a change in the observation distance. Then, by imaging the subject illuminated with the measurement light with the imaging element 25, a subject image including the spot SP that is the irradiation position of the measurement light can be obtained (refer to spots SP1, SP2, and SP3 in FIGS. 7 to 9). In the subject image, the position of the spot SP varies depending on a relationship between the optical axis Ax of the imaging optical system 24 and the optical axis of the measurement light Lm and the observation distance, but the number of pixels showing the same actual size (for example, 5 mm) increases in a case where the observation distance is shorter, and the number of pixels decreases in a case where the observation distance is longer.

In the length measurement mode, the light source processor 31 performs two types of light emission control: control for continuously emitting the measurement light Lm and control for pulse-emitting the measurement light Lm. In the control for continuously emitting the measurement light Lm, as shown in FIG. 4A, the light source processor 31 continuously emits the illumination light used for the overall illumination of the object to be observed and continuously emits the measurement light Lm. In this case, regarding a captured image obtained by the illumination of the illumination light and the measurement light, the spot SP is detected and the virtual scale is displayed.

Meanwhile, as shown in FIG. 4B, in the control for pulse-emitting the measurement light Lm, the light source processor 31 continuously emits the illumination light, while the measurement light Lm emits pulses. Therefore, the frames that emit light in the length measurement mode include an illumination light single emission frame FLx in which the measurement light is not emitted and the illumination light is independently emitted, and a measurement light emission frame FLy in which the illumination light and the measurement light are emitted. Then, in the length measurement mode, the position of the spot SP is detected from a first captured image obtained in the measurement light emission frame FLy, while the virtual scale is displayed on a second captured image obtained in the illumination light single emission frame FLx.

In addition, a solid line shown in a portion corresponding to the illumination light or the measurement light in FIG. 4 represents a light emission state in a certain frame. A period in which the solid line is present in a portion corresponding to "on" indicates a period in which the illumination light or the measurement light is emitted, and a period in which the solid line is present in a portion corresponding to "off" indicates a period in which bright light or the measurement light is not emitted.

As shown in FIG. 5, in order to recognize the position of the spot SP and set the virtual scale, the signal processing unit 41 of the extended processor device 17 comprises a first signal processing unit 50 that detects the position of the spot SP in the captured image, and a second signal processing unit 51 that sets the first virtual scale depending on the position of the spot SP. The extended processor device 17 is provided with a program memory (not shown) for storing programs related to various kinds of processing. The functions of the first signal processing unit 50 and the second signal processing unit 51 are realized by a central control unit (not shown) including an endoscope processor executing the programs in the program memory.

In addition, the captured image obtained in a case where the illumination light and the measurement light are always turned on includes the first captured image obtained in a case where both the illumination light and the measurement light in a case where the illumination light is always turned on while the measurement light is turned on or off, a still image obtained in a case where the still image acquisition instruction is given by operating the still image acquisition instruction switch 12g, or a still image automatically obtained by a still image automatic acquisition unit 66, in addition to a captured image obtained in a case where the illumination light and the measurement light are always turned on.

The first signal processing unit 50 comprises an irradiation position detection unit 52 that detects the irradiation position of the spot SP from the captured image. It is preferable that the irradiation position detection unit 52 acquires the center-of-gravity coordinates of the spot SP as the irradiation position of the spot SP.

The second signal processing unit 51 sets the first virtual scale as a virtual scale for measuring the size of the subject on the basis of the irradiation position of the spot SP and sets the scale display position of the first virtual scale. The first virtual scale is a scale in which the scale display position for displaying the scale varies depending on the position of the spot SP and the display mode varies depending on the scale display position. The second signal processing unit 51 sets the first virtual scale corresponding to the irradiation position of the spot SP by referring to a scale table 53 in which a virtual scale image of which the display mode varies depending on the irradiation position of the spot SP and the scale display position and the irradiation position of the spot are stored in association with each other in order to set the first virtual scale.

In the second signal processing unit 51, in a case where the length measurement mode is ON, any of the first virtual scale of which the scale display position varies and a second virtual scale of which the scale display position is fixed may be set as the virtual scale depending on the state of the zoom function. The second virtual scale is a scale in which the scale display position is fixed and the display mode is the same regardless of the position of the screen, or the display mode is changed depending on the position of the screen. This is because the distortion caused by the distortion aberration of the imaging optical system 24 varies depending on the position of the screen, so that the display mode (for example, the shape of the scale) is changed depending on the position of the screen.

The second signal processing unit 51 is provided with a zoom function recognition unit 54 that recognizes information on a state in which the zoom function is ON or OFF, or the magnification ratio. Additionally, the second signal processing unit 51 is provided with a second virtual scale setting unit 55 in order to set the second virtual scale.

Figure 6:
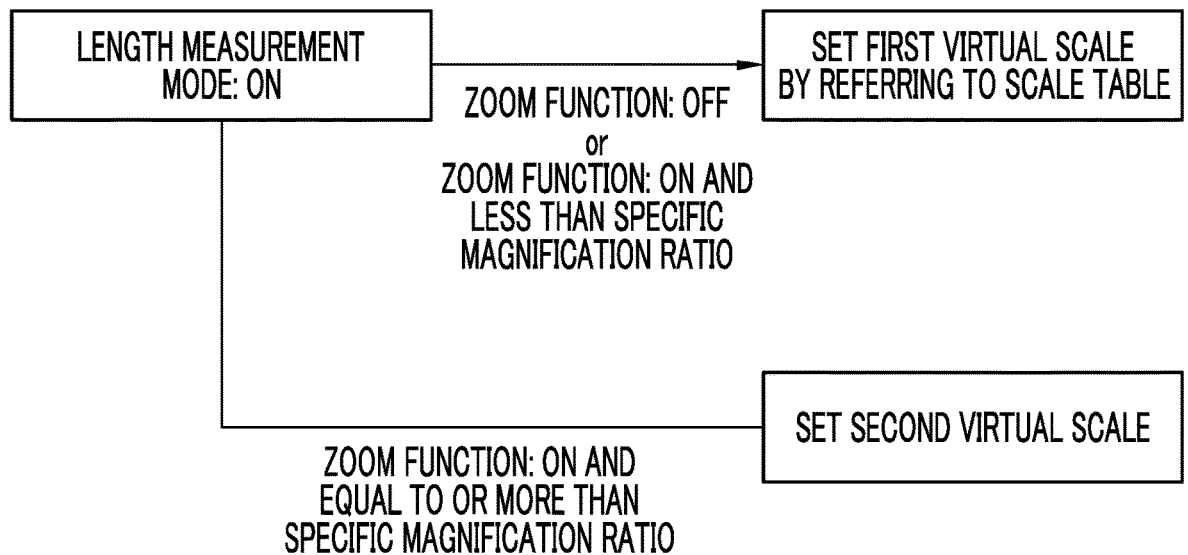
FIG. 6 is an explanatory diagram showing that a method of setting a virtual scale is changed depending on the state of a zoom function.

As shown in FIG. 6, in a case where the length measurement mode is set to ON and in a case where the zoom function is OFF or the zoom function is ON and the magnification ratio is less than the specific magnification ratio, the first virtual scale is set with reference to the scale table 53. On the other hand, in a case where the zoom function is ON and the magnification ratio is equal to or more than the specific magnification ratio, the second virtual scale is set. The specific magnification ratio is preferably a maximum magnification ratio to be tried with the zoom function.

Figure 7:
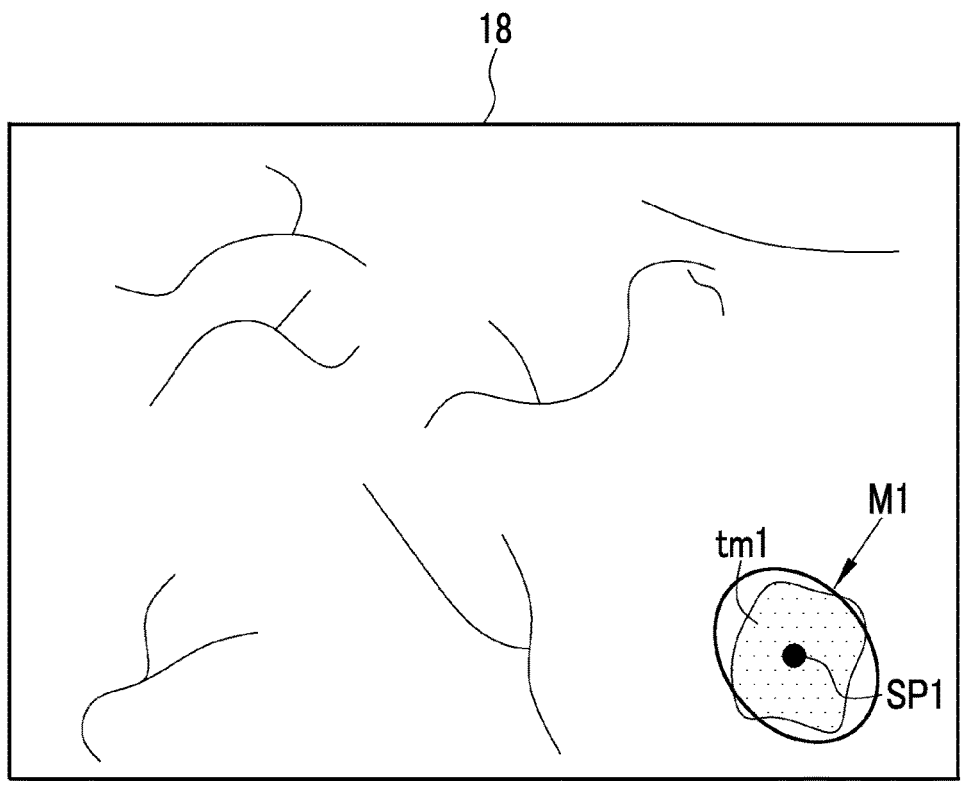
FIG. 7 is an image diagram showing a first virtual scale displayed in the case of a near end Px.

The first virtual scale varies in, for example, size or shape depending on the irradiation position and scale display position of the spot SP. A length measurement image on which the first virtual scale is superimposed is displayed on the extended display 18 around the spot SP. As the first virtual scale, for example, a circular measurement marker is used. In this case, as shown in FIG. 7, in a case where the observation distance is close to the near end Px (refer to FIG. 3), a first virtual scale M1 showing an actual size of 5 mm (the horizontal direction and the vertical direction of the captured image) is displayed in alignment with the center of the spot SP1 formed on a tumor tm1 of the subject.

Since the scale display position of the first virtual scale M1 is located at a peripheral portion of the captured image affected by the distortion caused by the imaging optical system 24, the first virtual scale M1 has an elliptical shape in accordance with the influence of the distortion and the like. Since the first virtual scale M1 described above substantially coincides with the range of the tumor tm1, the tumor tm1 can be measured to be about 5 mm. In addition, the spot may not be displayed on the captured image, and only the first virtual scale may be displayed.

Figure 8:
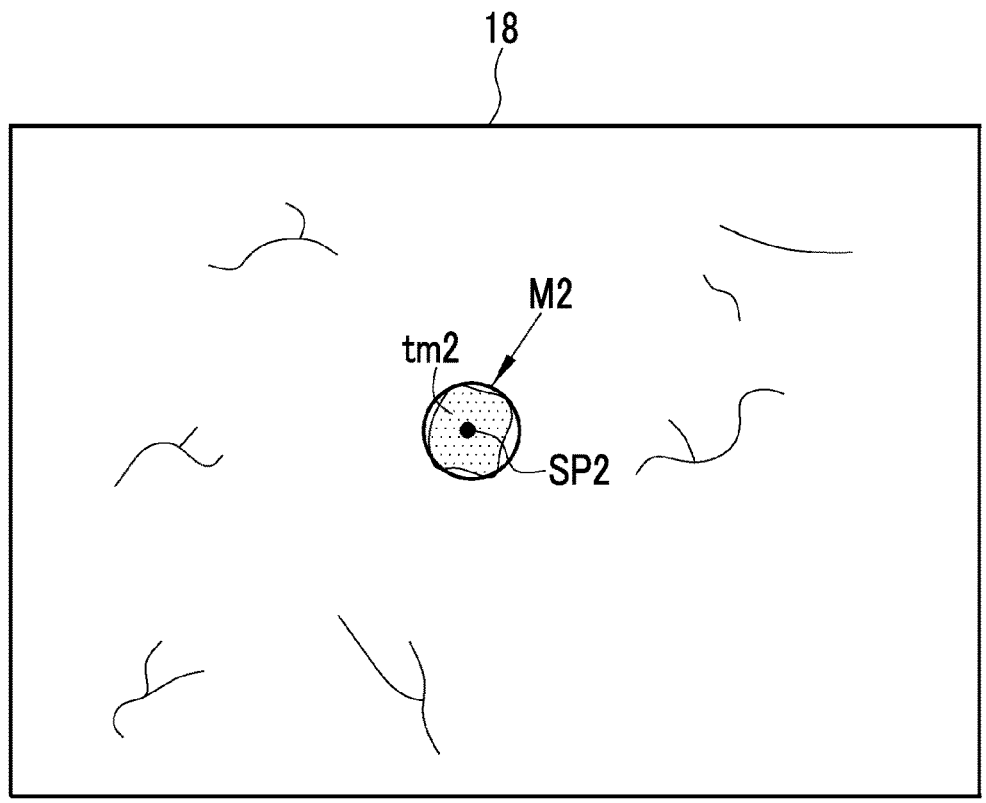
FIG. 8 is an image diagram showing the first virtual scale displayed in the case of a center vicinity Py.

Additionally, as shown in FIG. 8, in a case where the observation distance is close to the center vicinity Py, a first virtual scale M2 showing an actual size of 5 mm (the horizontal direction and the vertical direction of the captured image) is displayed in alignment with the center of the spot SP2 formed on a tumor tm2 of the subject. Since the scale display position of the first virtual scale M2 is located at a center portion of the captured image that is not easily affected by the distortion caused by the imaging optical system 24, the first virtual scale M2 has a circular shape without being affected by the distortion or the like.

Figure 9:
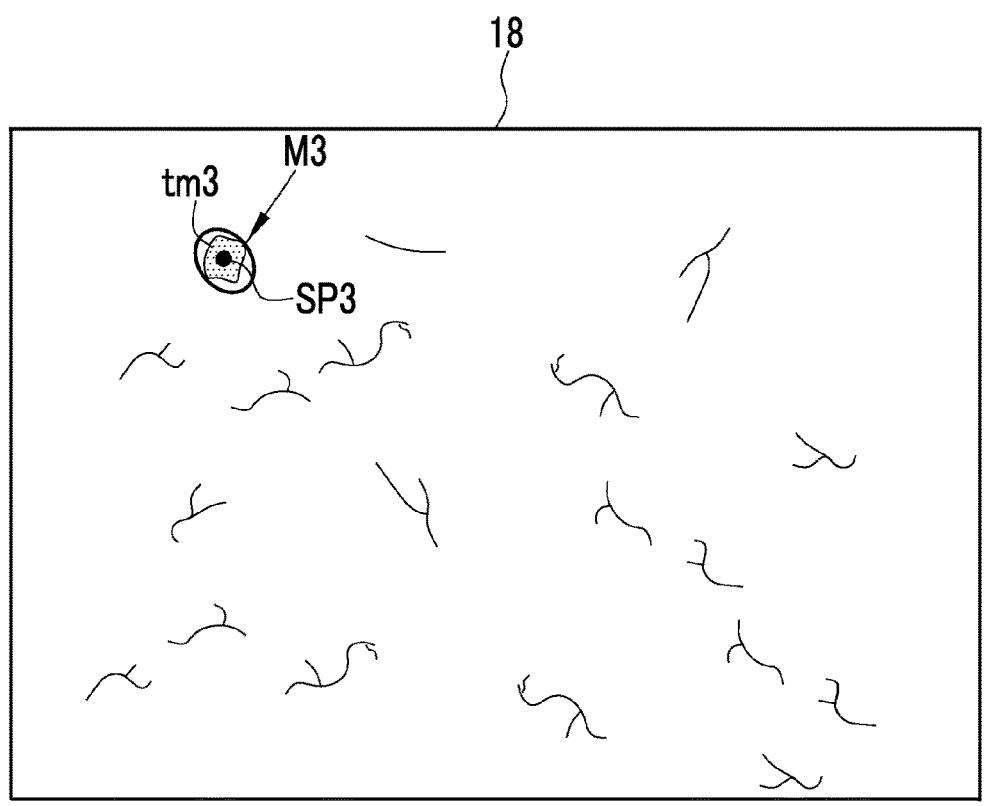
FIG. 9 is an image diagram showing the first virtual scale displayed in the case of a far end Pz.

Additionally, as shown in FIG. 9, a second virtual scale M3 showing an actual size of 5 mm (the horizontal direction and the vertical direction of the captured image) is displayed in alignment with the center of the spot SP3 formed on a tumor tm3 of the subject. Since the scale display position of the first virtual scale M3 is located at a peripheral portion of the captured image affected by the distortion caused by the imaging optical system 24, the first virtual scale M3 has an elliptical shape in accordance with the influence of the distortion and the like. As shown in the above FIGS. 7 to 9, the size of the first virtual scale corresponding to the same actual size of 5 mm becomes smaller as the observation distance becomes longer. Additionally, the shape of the first virtual scale varies depending on the scale display position in accordance with the influence of the distortion caused by the imaging optical system 24.

In addition, in FIGS. 7 to 9, the center of the spot SP and the center of the scale are displayed so as to coincide with each other, but in a case where there is no problem in terms of measurement accuracy, the first virtual scale may be displayed at a position away from the spot SP. However, even in this case, it is preferable to display the first virtual scale in the vicinity of the spot. Additionally, the first virtual scale in a state where the distortion aberration of the captured image is corrected and not deformed instead of deforming and displaying the first virtual scale may be displayed on the corrected captured image.

Additionally, in FIGS. 7 to 9, the first virtual scale corresponding to the actual size of the subject that is 5 mm is displayed, but the actual size of the subject is an optional value (for example, 2 mm, 3 mm, 10 mm, or the like) may be set depending on the object to be observed and an observation purpose). Additionally, in FIGS. 7 to 9, the first virtual scale has a substantially circular shape, but as shown in FIG. 10, may have a cross shape in which a vertical line and a horizontal line intersect each other. Additionally, a graduated cross shape in which graduations Mx are attached to at least one of the vertical line or horizontal line of the cross shape may be used. Additionally, as the first virtual scale, a distorted cross shape in which at least one of a vertical line or a horizontal line is inclined may be used. Additionally, the first virtual scale may be a circle and cross shape in which a cross shape and a circle are combined with each other. In addition, the first virtual scale may have a measurement point group shape in which a plurality of measurement point EPs corresponding to the actual size from the spot are combined with each other. Additionally, the number of first virtual scales may be one or multiple, and the color of the first virtual scale may be changed depending on the actual size.

In addition, as the first virtual scale, as shown in FIG. 11, three concentric first virtual scales M4A, M4B, and M4C (the sizes are 2 mm, 5 mm, and 10 mm in diameter, respectively) having different sizes may be displayed on the captured image as a center around a spot SP4 formed on a tumor tm4. Since these three concentric virtual scales display a plurality of virtual scales, the time and effort for switching can be saved, and measurement is possible even in a case where the subject has a non-linear shape. In addition, in a case where the plurality of concentric virtual scales are displayed around the spot, instead of specifying size and color for each virtual scale, a combination of a plurality of conditions may be prepared in advance so that a selection can be made from the combination.

Figure 12:
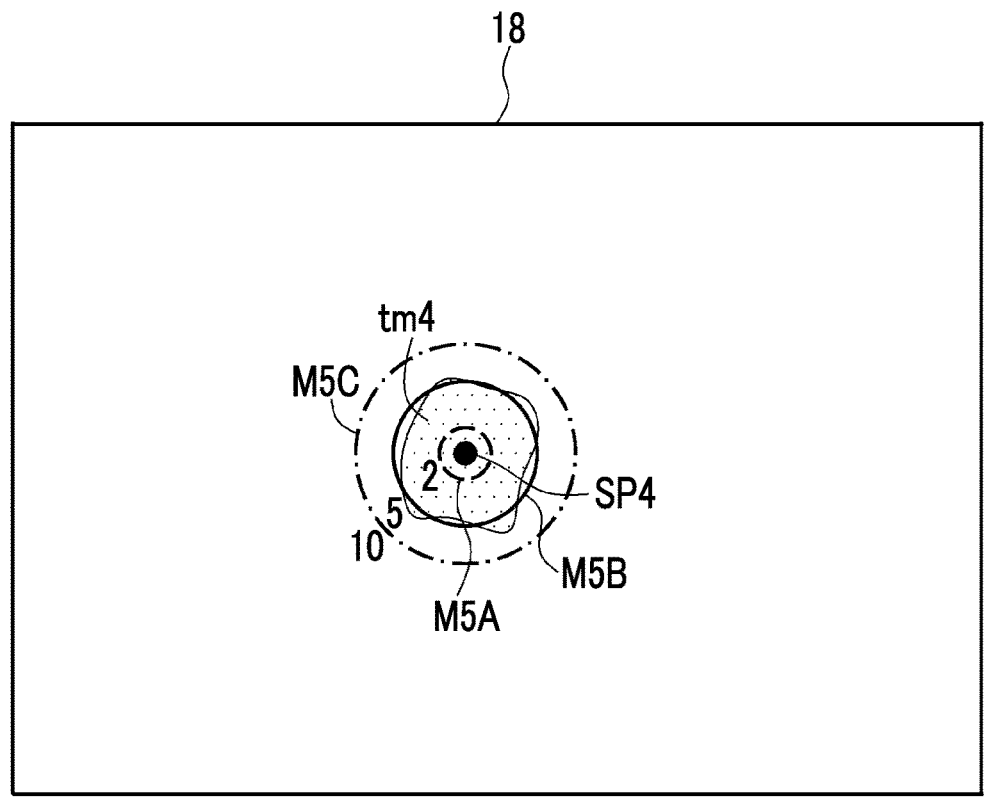
FIG. 12 is an explanatory diagram showing the first virtual scales having different colors.

In FIG. 11, all the three first concentric virtual scales are displayed in the same color (black), but in a case where a plurality of concentric scales are displayed, a plurality of colored concentric circles of which the colors are changed depending on the virtual scales may be used. As shown in FIG. 12, a first virtual scale M5A is displayed by a dotted line representing red, a second virtual scale M5B is displayed by a solid line representing blue, and a third virtual scale MSC is displayed by an alternate long and short dash line representing white. By changing the colors of the first virtual scales in this way, the discriminability is improved and the measurement can be easily performed.

Figure 13:
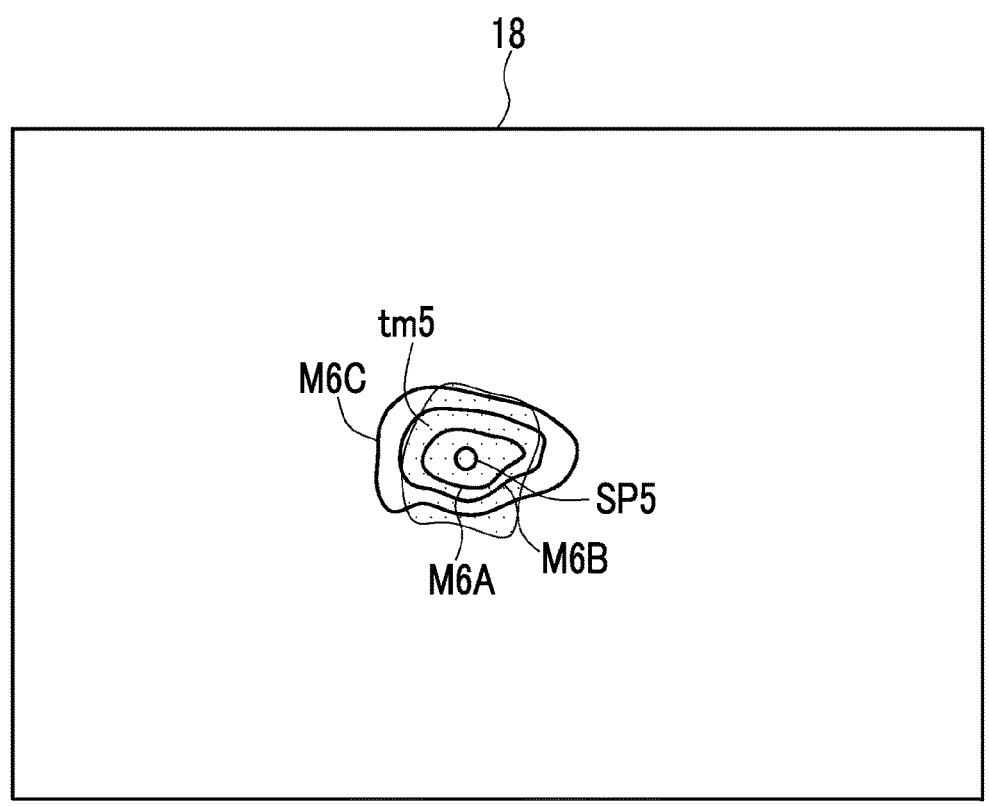
FIG. 13 is an explanatory diagram showing the first virtual scales having distorted concentric shapes.

Additionally, as the first virtual scale, in addition to the plurality of concentric virtual scales, as shown in FIG. 13, a plurality of distorted concentric first virtual scales in which the respective concentric circles are distorted may be used. In this case, distorted concentric first virtual scale M6A, virtual scale M6B, and virtual scale M6C are displayed in the captured image around the spot SP5 formed on the tumor tm5.

Figure 14:
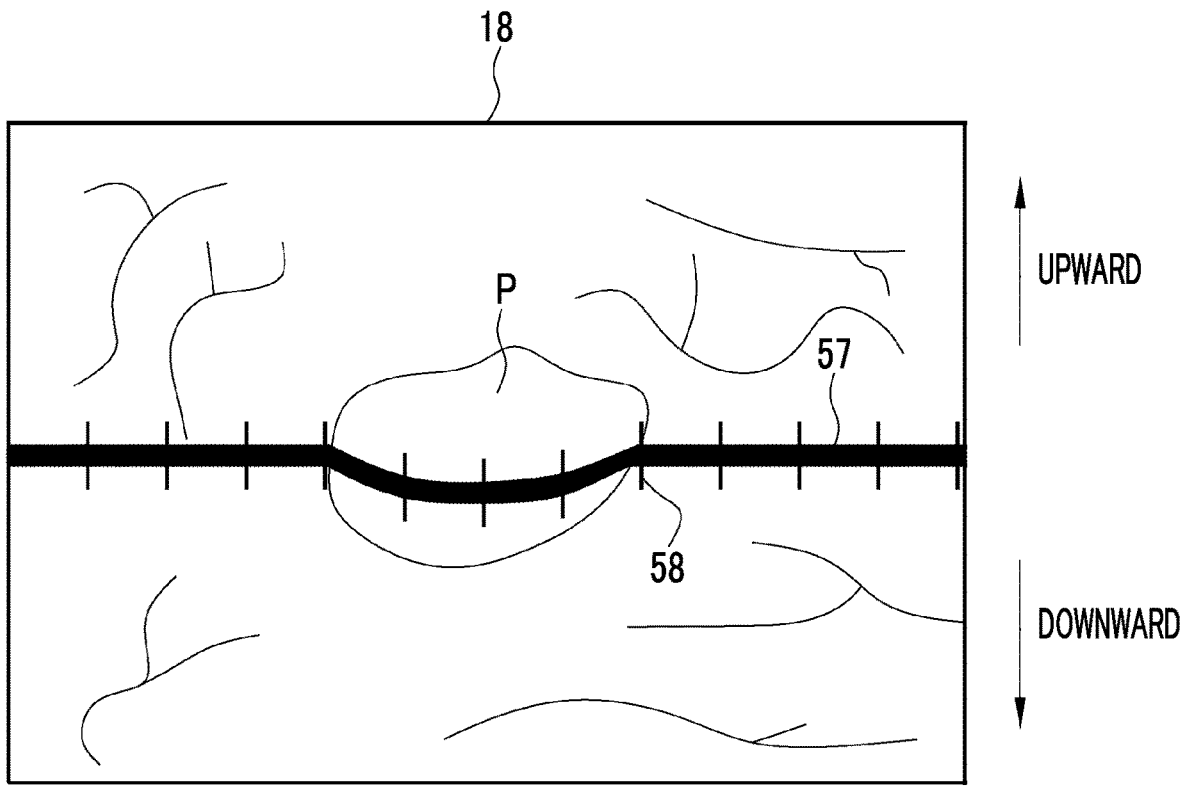
FIG. 14 is an explanatory diagram showing the first virtual scale including intersection lines and graduations.

In addition, as for the measurement light, the light formed as a spot in a case where the subject is irradiated is used, but other light may be used. For example, in a case where the subject is irradiated, as shown in FIG. 14, a planar measurement light formed as an intersection line 57 on the subject may be used. In this case, as the first virtual scale, a scale including the intersection line 57 and graduations 58 serving as indexes of the size of the subject (for example, polyp P) on the intersection line 57 is generated.

In a case where the planar measurement light is used, the irradiation position detection unit 52 detects the position (the irradiation position of the measurement light) of the intersection line 57. As the intersection line 57 is located on the lower side, the observation distance is closer, and as the intersection line 57 is located on the upper side, the observation distance is farther. For that reason, as the intersection line 57 is located on the lower side, the interval between the graduations 58 is larger, and as the intersection line 67 is located on the upper side, the interval between the graduations 58 is smaller.

Figure 15:
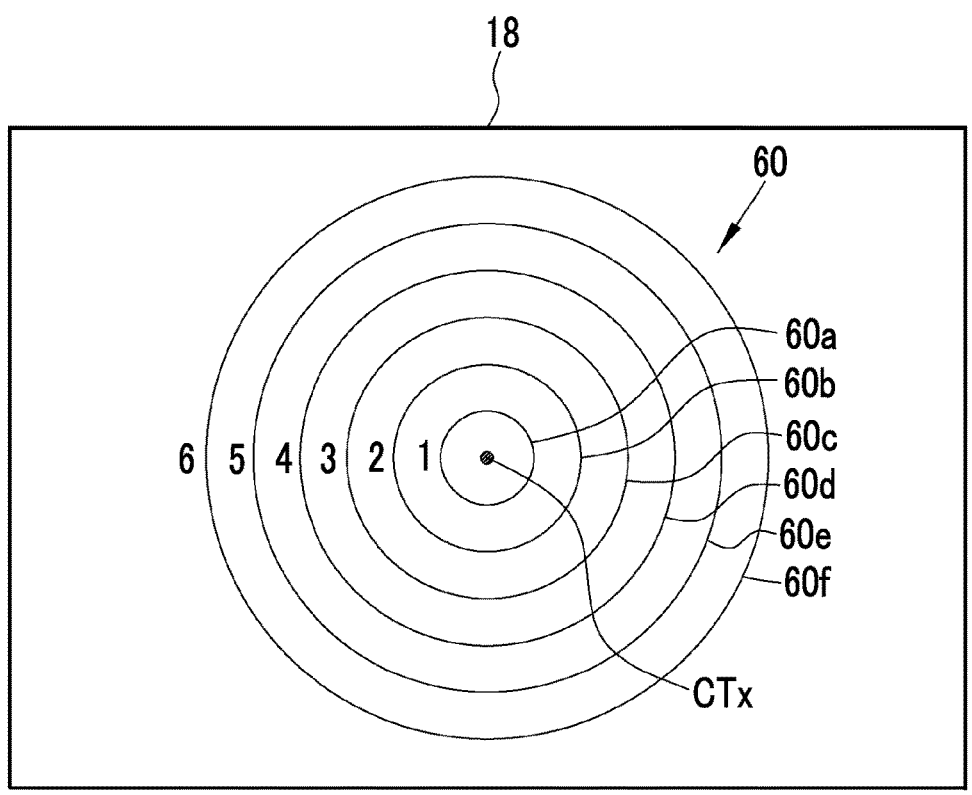
FIG. 15 is an image diagram showing a concentric second virtual scale.

A specific example of the second virtual scale used in a case where the zoom function is equal to or more than the specific magnification ratio (for example, the maximum magnification ratio) will be described below. For example, as shown in FIG. 15, a second virtual scale 60 constituted of six concentric circles may be used. The second virtual scale 60 includes a circular scale 60a showing a size of 1 mm, a circular scale 60b showing a size of 2 mm, a circular scale 60c showing a size of 3 mm, a circular scale 60d showing a size of 4 mm, a circular scale 60e having a size of 5 mm, a circular scale 60f showing a size of 6 mm, and these circular scales 60a to 60f are displayed around the same center CTx. The scale display position of the second virtual scale 60 is fixed with the center CTx as the center of the screen of the extended display 18. For that reason, information on the position of the spot SP is not required for the display of the second virtual scale 60 (the same applies to the second virtual scales 62 and 64 below).

Here, it is known that the absolute value of the distortion aberration of the imaging optical system 24 in a case where the zoom function is ON is smaller than the absolute value of the distortion aberration of the imaging optical system 24 in a case where the zoom function is OFF. Specifically, the absolute value of distortion aberration in the case of the maximum magnification ratio is equal to or less than 10%. For that reason, in a case where the zoom function is equal to or more the specific magnification ratio, such as the maximum magnification ratio, the shape distortion at a peripheral portion of the screen is small. Therefore, it is not necessary to deform the shape of the scale depending on the position of the screen as in a case where the zoom function is OFF (refer to FIGS. 7 and 9). For that reason, in the second virtual scale 60, unlike the circular scales 60e and 60f, the deformation according to the position of the screen is not performed on the scale located in the peripheral portion of the screen.

Figure 16:
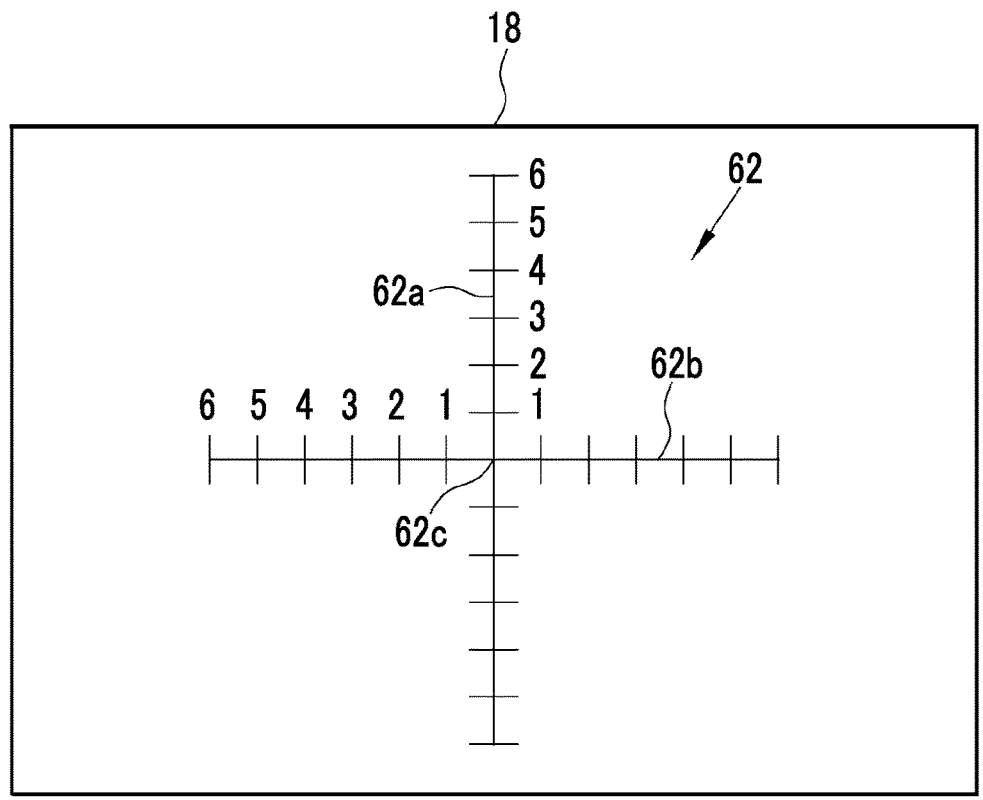
FIG. 16 is an image diagram showing a cross-shaped second virtual scale.

Additionally, as shown in FIG. 16, a cross-shaped second virtual scale 62 in which memories are provided at intervals of 1 mm on a vertical axis 62a and a horizontal axis 62b, respectively, may be used. In the second virtual scale 62, the vertical axis 62a is provided with graduations at intervals of 1 mm, and the horizontal axis 62b is also provided with graduations at intervals of 1 mm. The scale display position of the second virtual scale 62 is fixed with an intersection point 62c between the vertical axis 62a and the horizontal axis 62b as the center of the screen of the extended display 18. Even in the second virtual scale 62, in a case where the zoom function is equal to or more than the specific magnification ratio, the distance between the graduations of the portion of the vertical axis 62a and the horizontal axis 62 located at the peripheral portion of the screen is changed depending on the position of the screen.

Figure 17:
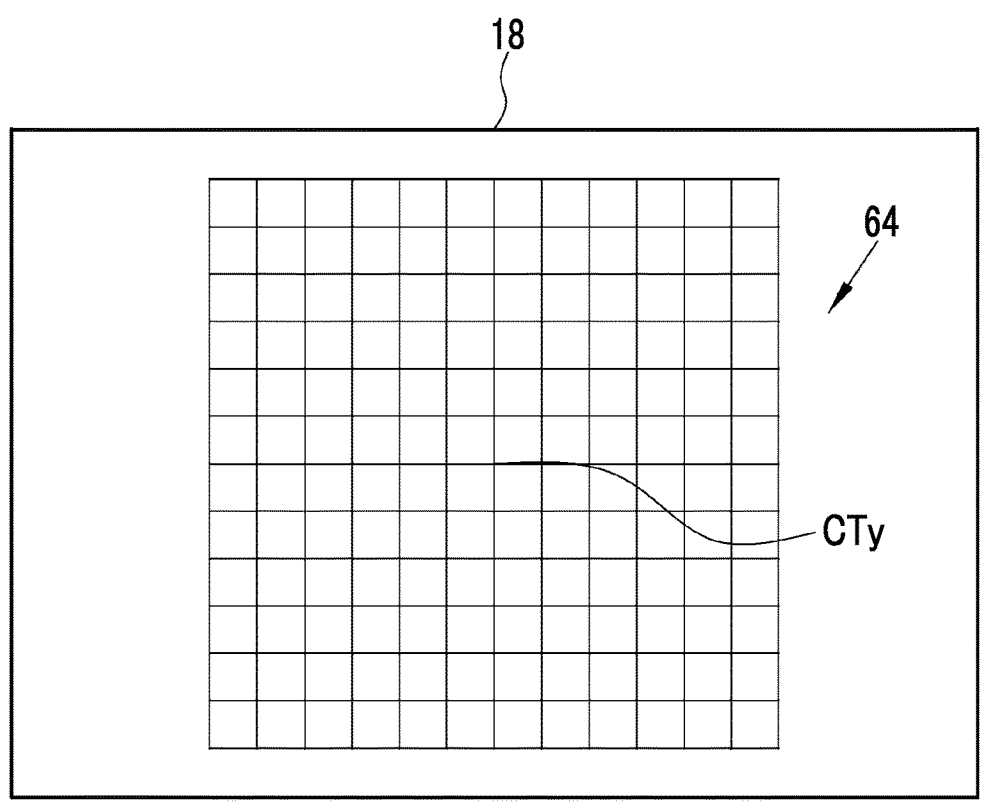
FIG. 17 is an image diagram showing a square grid-shaped second virtual scale.

Additionally, as shown in FIG. 17, a second virtual scale 64 having a square grid shape in which square grids having a length and width of 1 mm are arranged in the vertical direction and the horizontal direction may be used. The scale display position of the second virtual scale 64 is fixed with a center Cty as the center of the screen of the extended display 18. Even in the second virtual scale 64, in a case where the zoom function is equal to or more than the specific magnification ratio, the shape of the square grid of the portion located at the peripheral portion of the screen is not deformed depending on the position of the screen.

Figure 18:
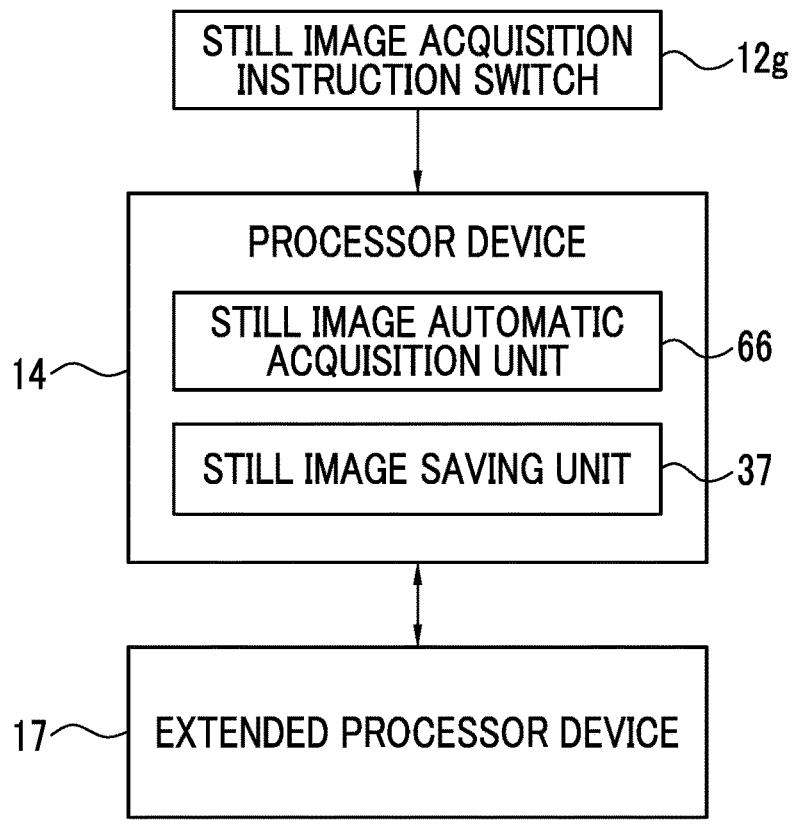
FIG. 18 is a block diagram showing functions for manually or automatically acquiring a still image.

In the endoscope system 10, in a case where the length measurement mode is set, a still image is manually or automatically acquired. As shown in FIG. 18, in a case where the still image is manually acquired, the still image acquisition instruction is transmitted to the processor device 14 by the user operating the still image acquisition instruction switch 12g. In the processor device 14, the still image at the timing when the still image acquisition instruction is given is associated with the length measurement information at the timing when the still image acquisition instruction is given, and is stored in the still image saving unit 37. The length measurement information includes information obtained by quantifying the size of the measurement object on the basis of the first virtual scale or the second virtual scale, in addition to the positional information of the spot SP and the information of the first virtual scale, the second virtual scale, or the like.

On the other hand, in a case where the still image is automatically acquired, the still image automatic acquisition unit 66 in the processor device 14 monitors whether or not the captured image satisfies an automatic acquisition target image, and automatically saves the captured image corresponding to the automatic acquisition target image as a still image in the still image saving unit 37. The automatic acquisition target image includes a treatment image related to treatment such as endoscopic submucosal dissection (ESD), in addition to a specific observation image related to a specific lesion. The automatically acquired still image is stored in the still image saving unit 37 in association with the length measurement information at the timing when the automatic acquisition is performed, similarly to the case of the manual acquisition. In addition, the still image automatic acquisition unit 66 may be a learned model machine-learned with teacher image data including the automatic acquisition target image. The machine learning includes supervised learning, semi-supervised learning, unsupervised learning, reinforcement learning, deep reinforcement learning, learning using a neural network, deep learning, and the like.

Figure 19:
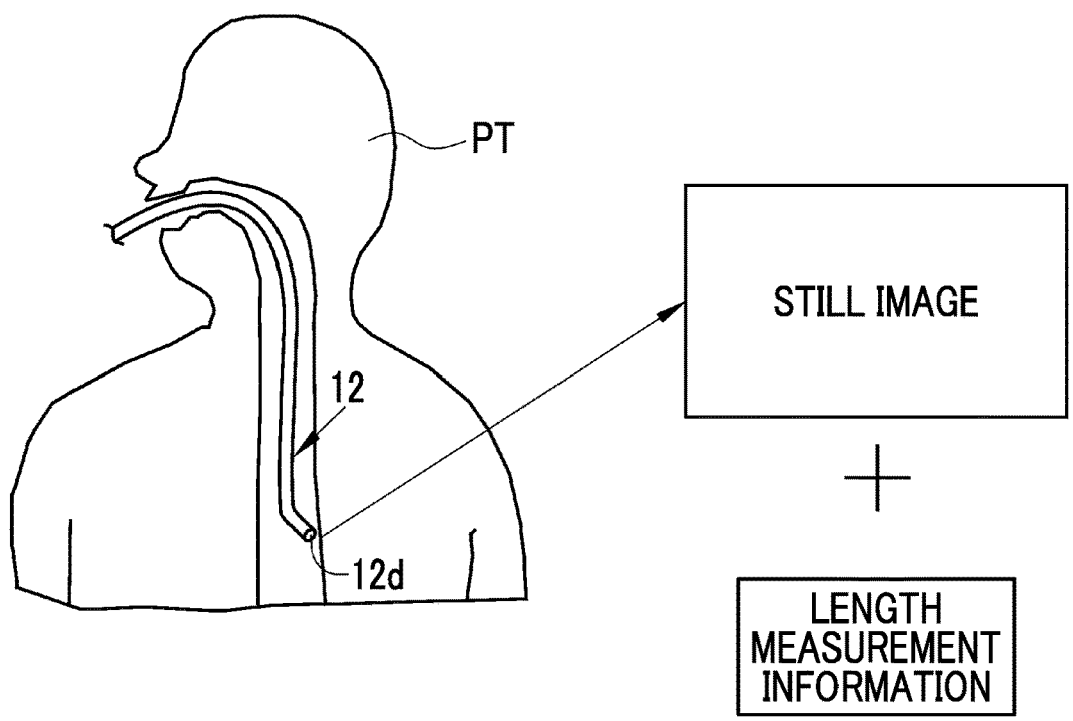
FIG. 19 is an explanatory diagram regarding the acquisition of the still image during treatment.

In addition, as for the acquisition of the still image in a case where the treatment such as ESD is performed, it is preferable to acquire both a still image at the time of the treatment and the still image of a removed specimen in order to create a report after the treatment. Specifically, as shown in FIG. 19, the still image is manually or automatically acquired while the gastrointestinal tract of a patient PT is imaged by the endoscope 12. In the length measurement mode, the length measurement information is associated with the acquired still image and stored in the still image saving unit 37. The imaging of the gastrointestinal tract includes treatments such as ESD in addition to the observation of lesions.

Figure 20:
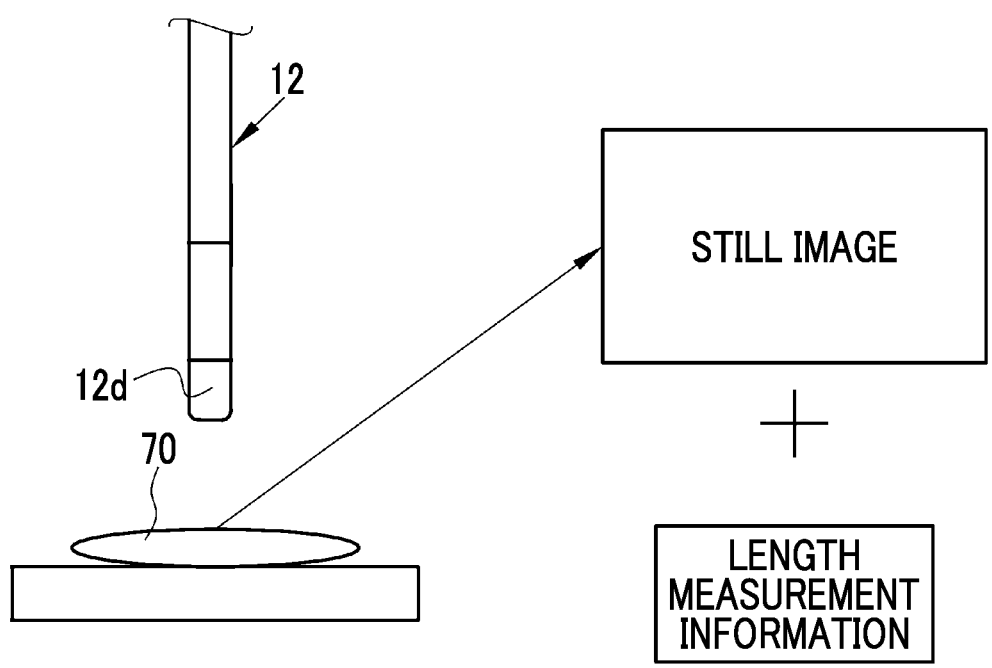
FIG. 20 is an explanatory diagram regarding the acquisition of a still image of a specimen removed by the treatment.

On the other hand, as shown in FIG. 20, in a case where the treatment such as ESD is performed, after the endoscope 12 is removed from the patient, a still image of the removed specimen 70 removed by the treatment is manually or automatically acquired by the endoscope 12. In the length measurement mode, the length measurement information is associated with the acquired still image and stored in the still image saving unit 37. The still image at the time of the above treatment and the still image of the specimen are transmitted to the endoscopy service support device 100 via the network NT. In addition, in the processor device 14, as for the still image saved in the still image saving unit 37, in order to identify an internal still image or an external still image, the still image at the time of the treatment may be tagged with an internal still image tag, and the still image of the removed specimen may be tagged with an external still image tag.

Figure 21:
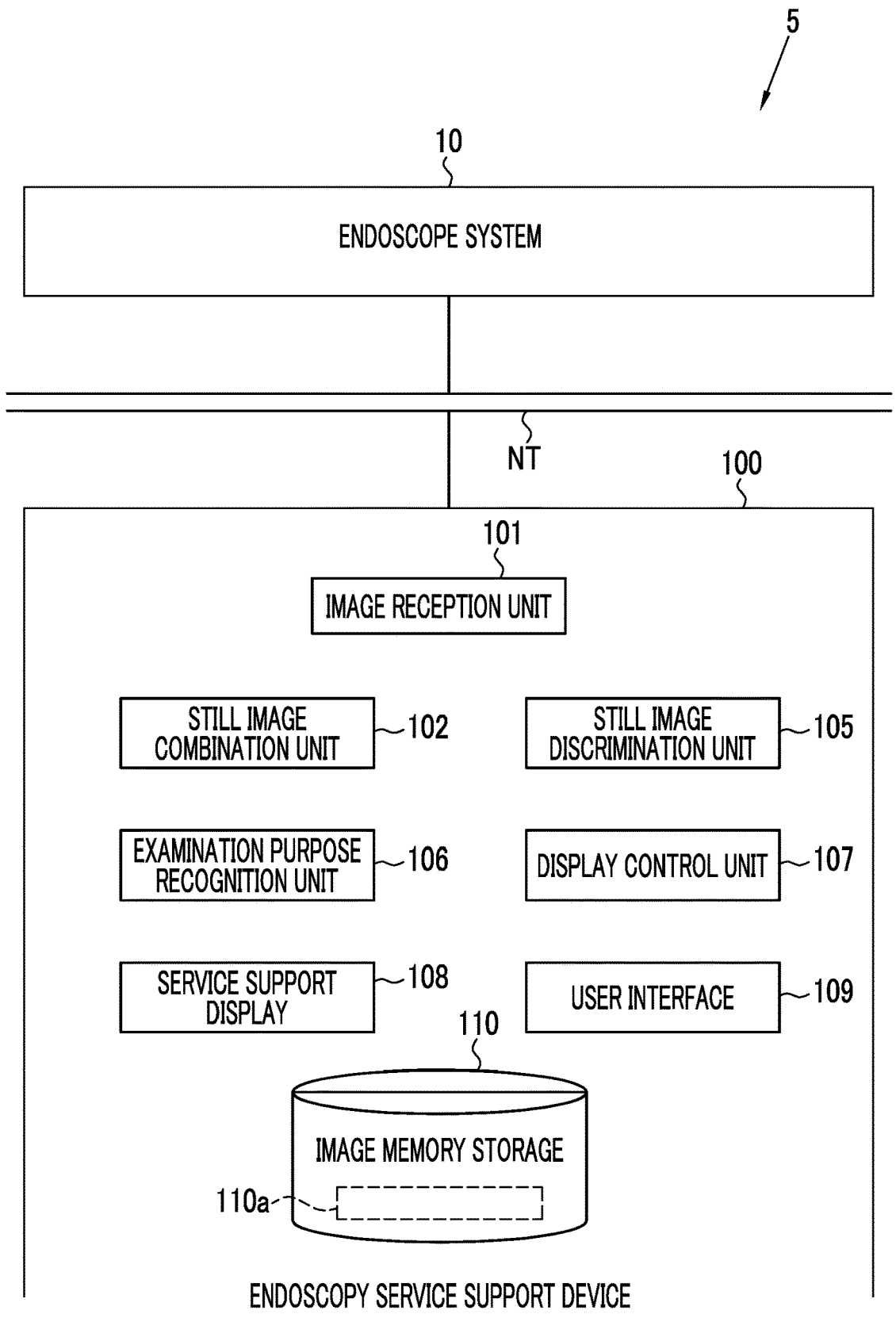
FIG. 21 is a schematic diagram of the endoscopy service support system showing respective functions of an endoscopy service support device.

As shown in FIG. 21, the endoscopy service support device 100 includes an image reception unit 101, a still image combination unit 102, a still image discrimination unit 105, an examination purpose recognition unit 106, a display control unit 107, a service support display 108, a user interface 109 and an image memory storage 110. The endoscopy service support device 100 is provided with a program memory (not shown) for storing programs related to various kinds of processing. By executing a program in the program memory by a central control unit (not shown) constituted of a processor for service support, the functions of the image reception unit 101, the still image combination unit 102, the still image discrimination unit 105, the examination purpose recognition unit 106, and the display control unit 107 are realized.

The image reception unit 101 receives the still image acquired by the endoscope system 10. The received still image is stored in the image memory storage 110. Still images are sequentially read from the image memory storage 110 in response to an instruction to create a medical document such as a report. In addition, the still image is preferably a still image stored in the still image saving unit 37. In addition, the user interface 109 preferably has the same function as the user interface 16.

In a case where the endoscopy service support device 100 gives an instruction to create a medical document such as a report related to ESD treatment, a still image used for creating the medical document is read out from the image memory storage 110. The still image combination unit 102 performs still image collation processing for collating the internal still image with the external still image out of the still images read from the image memory storage 110 and combines the internal still image with the external still image in at least the still image collation processing. The combined internal still image and external still image are stored in a case image folder 110*a* in the image memory storage 110 and used for creating a medical document or the like. It is preferable that the still image collation processing is performed by pattern matching using the brightness and color information of the internal still image and the external still image, or the like.

It is preferable that the external still image is a still image tagged with an internal still image by the endoscope system 10, and the external still image is a still image tagged with an external still image by the endoscope system 10. In a case where a still image is tagged with the external still image or the external still image in the endoscope system 10, the still image discrimination unit 105 performs discrimination between the internal still image or the external still image.

The still image discrimination unit 105 discriminates between the internal still image and the external still image on the basis of the feature quantity of a still image such as brightness and color information. In addition, the still image discrimination unit 105 may be the learned model machine-learned with the teacher image data. The machine learning includes supervised learning, semi-supervised learning, unsupervised learning, reinforcement learning, deep reinforcement learning, learning using a neural network, deep learning, and the like.

In the still image combination unit 102, in addition to the still image collation processing, the examination purpose discrimination processing of whether or not the examination purposes match each other between the internal still image and the external still image may be performed, and the internal still image and the external still image may be combined with each other on the basis of the still image collation processing and the examination purpose discrimination processing. In this case, it is necessary that the examination purpose is associated with the internal still image or the external still image. The examination purpose preferably includes observation and treatment. Specifically, in a case where the internal still image and the external still image of which the examination purposes are the treatment are combined with each other, the still image combination unit 102 combines the internal still image and the external still image of which the examination purposes are treatment with each other, out of the internal still images that match the external still image, as a result of the still image collation processing.

In addition, it is preferable that the examination purpose recognition unit 106 automatically recognizes the examination purpose of the internal still image and the external still image. The examination purpose recognition unit 106 recognizes the examination purpose on the basis of the feature amount of the internal still image or the external still image such as the presence or absence of the treatment tool. The examination purpose is associated with the internal still image or the external still image on the basis of the recognition result. As will be described below, the user may manually select the examination purpose on an examination purpose selection screen (refer to FIG. 24) displayed on the service support display 108. In addition, the examination purpose recognition unit 106 may be the learned model machine-learned with the teacher image data. The machine learning includes supervised learning, semi-supervised learning, unsupervised learning, reinforcement learning, deep reinforcement learning, learning using a neural network, deep learning, and the like.

Figure 22:
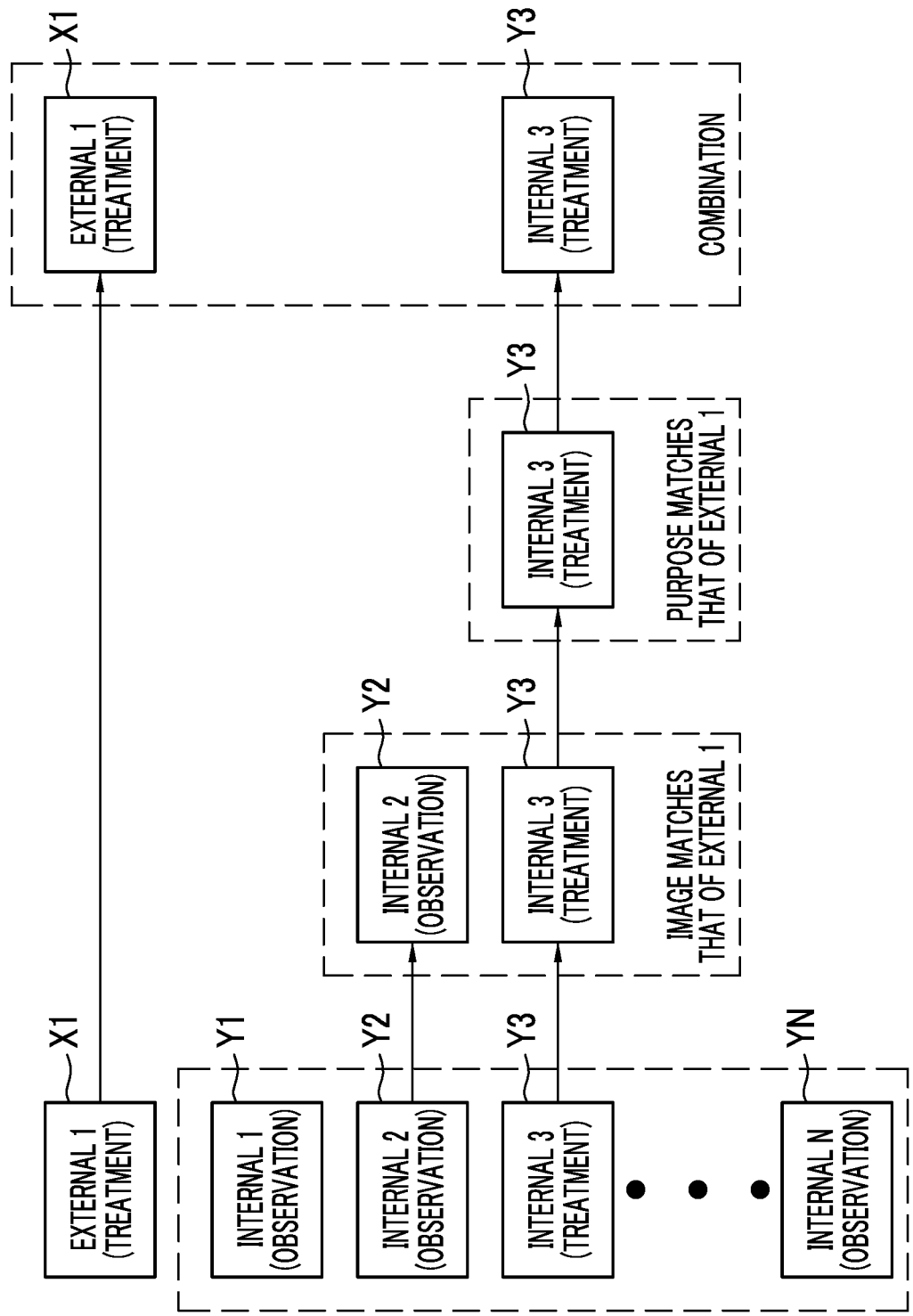
FIG. 22 is an explanatory diagram showing that an internal still image and an external still image are combined with each other by still image collation processing and examination purpose discrimination processing.

A specific example in a case where the internal still image and the external still image are combined with each other in the still image combination unit 102 on the basis of the still image collation processing and the examination purpose discrimination processing will be described below. As shown in FIG. 22, in a case where an external still image X1 (external 1 (treatment)) of which the examination purpose is treatment is present as the external still image and an internal still image Y1 of which the examination purpose is observation (internal 1 (observation)), an internal still image Y2 (internal 2 (observation)) of which the examination purpose is the observation, an internal still image Y3 (internal 3 (treatment)) of which the examination purpose is the treatment, . . . , an internal still image YN (internal N (observation)) of which the examination purpose is the observation are present as the internal still images, first, the internal still image Y2 and the internal still image Y3 are selected as the internal still images that match the external still image X1 by the still image collation processing. Next, the internal still image Y3 that matches the external still image X1 of which the examination purpose is the treatment out of the internal still image Y2 and the internal still image Y3 is selected by the examination purpose discrimination processing. As described above, the still image combination unit 102 combines the external still image X1 with the internal still image Y3.

In the still image combination unit 102, in addition to the still image collation processing, the length measurement information discrimination processing of whether or not the length measurement information matches may be performed, and the internal still image and the external still image may be combined with each other on the basis of the still image collation processing and the length measurement information discrimination processing. In this case, it is necessary that the length measurement information is associated with the internal still image and the external still image, respectively. Specifically, the still image combination unit 102 combines the internal still image and the external still image of which the length measurement information matches that of the external still image with each other, out of the internal still images that match the external still image, as a result of the still image collation processing. In addition, in order to discriminate whether the length measurement information matches or does not match in the length measurement information discrimination processing, it is preferable that the length measurement information is size information in which a length measurement object is manually or automatically quantified on the basis of the first virtual scale or the second virtual scale.

Figure 23:
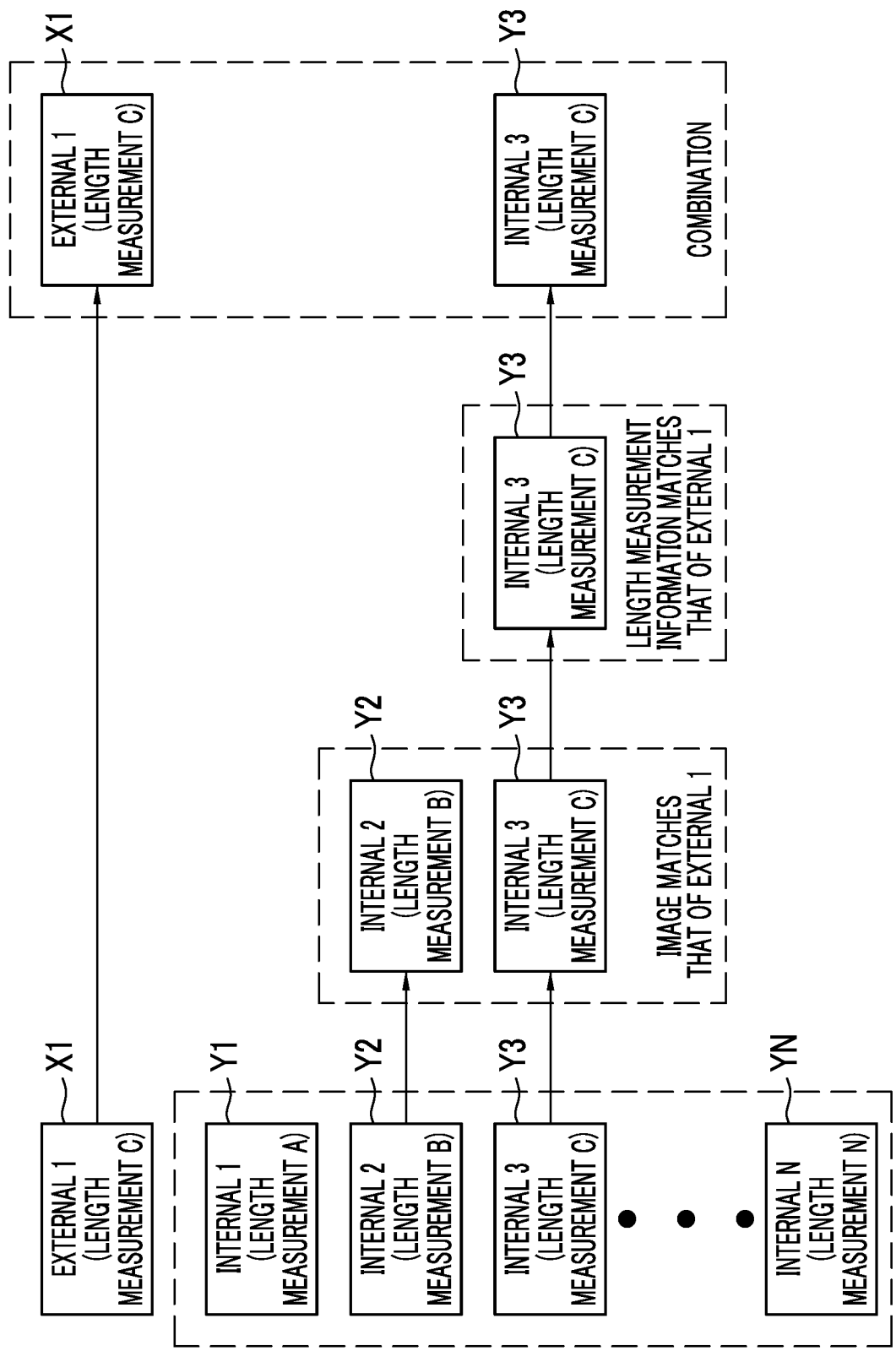
FIG. 23 is an explanatory diagram showing that the internal still image and the external still image are combined with each other by the still image collation processing and length measurement information discrimination processing.

A specific example in a case where the internal still image and the external still image are combined with each other in the still image combination unit 102 on the basis of the still image collation processing and the length measurement information discrimination processing will be described below. As shown in FIG. 23, in a case where an external still image X1 (external 1 (length measurement C)) of which the length measurement information is length measurement C is present as the external still image and an internal still image Y1 (internal 1 (length measurement A)) of which the length measurement information is length measurement A, an internal still image Y2 (internal 2 (length measurement B)) of which the length measurement information is length measurement B, an internal still image Y3 (internal 3 (length measurement C)) of which the length measurement information is length measurement C, . . . , an internal still image YN (internal N (length measurement N)) of which the length measurement information is length measurement N are present as the internal still images, the internal still image Y2 and the internal still image Y3 are selected as the internal still images that match the external still image X1 by the still image collation processing. Next, the internal still image Y3 that matches the external still image X1 of which the length measurement information is the treatment out of the internal still image Y2 and the internal still image Y3 is selected by the length measurement information discrimination processing. As described above, the still image combination unit 102 combines the external still image X1 with the internal still image Y3.

Figure 24:
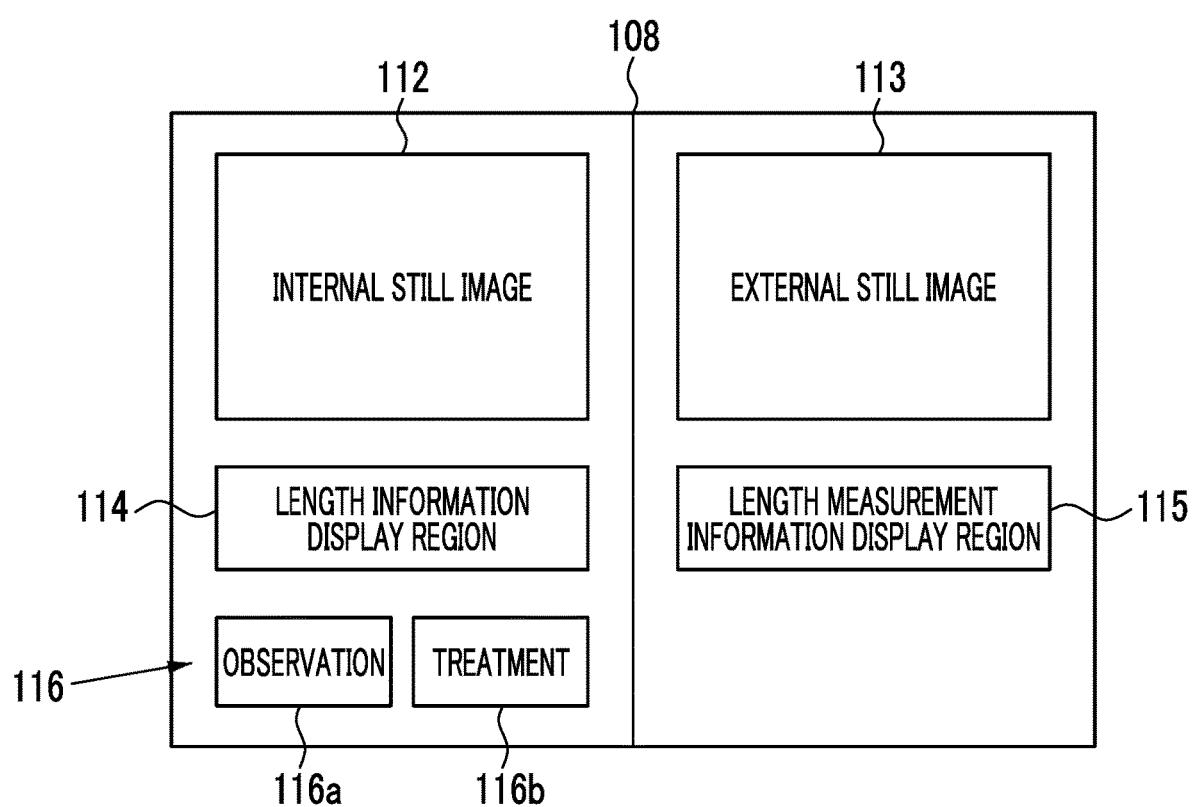
FIG. 24 is an image diagram of a service support display for displaying the internal still image and the external still image.

As shown in FIG. 24, the display control unit 103 displays an internal still image 112 and an external still image 113 combined with each other by the still image combination unit 102 on the service support display 108. The user creates a medical document such as a report on treatment by using the internal still image 112 and the external still image 113.

The service support display 108 is provided with length measurement information display regions 114 and 115 for displaying the length measurement information of the internal still image or the external still image. For example, it is preferable that the size of a removal range related to a region from which the specimen is removed is displayed on the length measurement information display region 114 and the size of the specimen removed by treatment such as ESD is displayed on the length measurement information display region 115.

Additionally, the service support display 108 is provided with an examination purpose selection screen 116 so that the user can manually input the examination purpose for the internal still image. The examination purpose selection screen 116 includes an observation selection icon 116a for selecting the observation and a treatment selection icon 116b for selecting the treatment. In a case where the examination purpose is manually input, the user interface 109 is operated to switch to an examination purpose input mode. In the examination purpose input mode, the internal still image out of the still images stored in the image memory storage 110 are sequentially displayed in a display region of an endoscopy service internal still image. The user operates the user interface 109 on the sequentially displayed internal still images, clicks the observation selection icon 116a or the treatment selection icon 116b, and selects the observation or the treatment. By the selection operation, the examination purpose of the observation or the treatment is associated with the internal still image.

Figure 25:
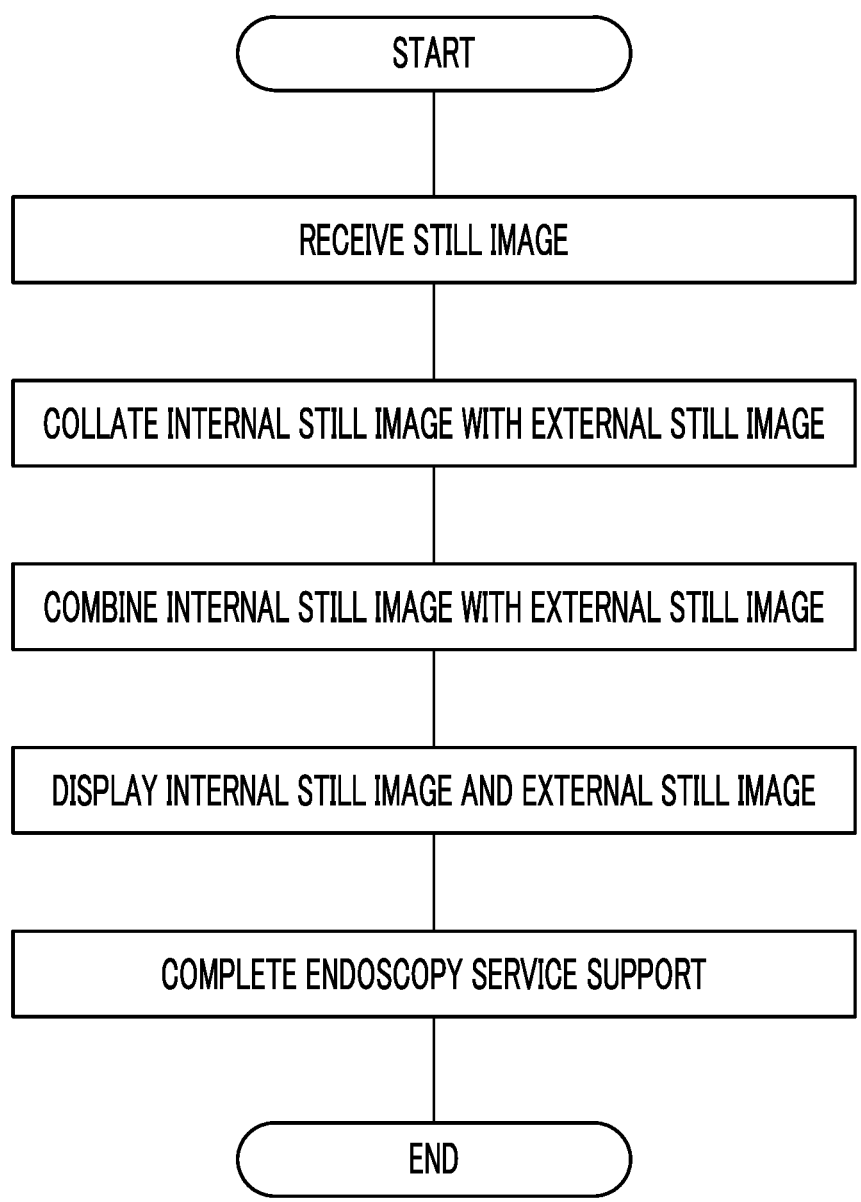
FIG. 25 is a flowchart showing a series of flows regarding endoscopy service support.

Next, a series of flows in which the internal still image and the external still image acquired by the endoscope system 10 are combined with each other and displayed on the service support display 108 in the endoscopy service support device 100 will be described along a flowchart of FIG. 25. According to the operation of the user interface 109, the image reception unit 101 receives a still image via the network NT from the endoscope system 10. The received still image is stored in the image memory storage 110.

In a case where an instruction for endoscopy service support such as the creation of a medical document is given by operating the user interface 109, the still image combination unit 102 reads the still image from the image memory storage 110. The still image combination unit 102 performs the still image collation processing for collating the internal still image with the external still image out of the still images and combines the internal still image and the external still image with each other on the basis of at least the result of the still image collation processing. The display control unit 107 displays the combined internal still image and external still image on the service support display 108. Additionally, the combined internal still image and external still image are stored in the case image folder 110a in the image memory storage 110. In a case where the input of the opinion or the like by the user is completed, the user operates the user interface 109 to complete the endoscopy service support.

Figure 26:
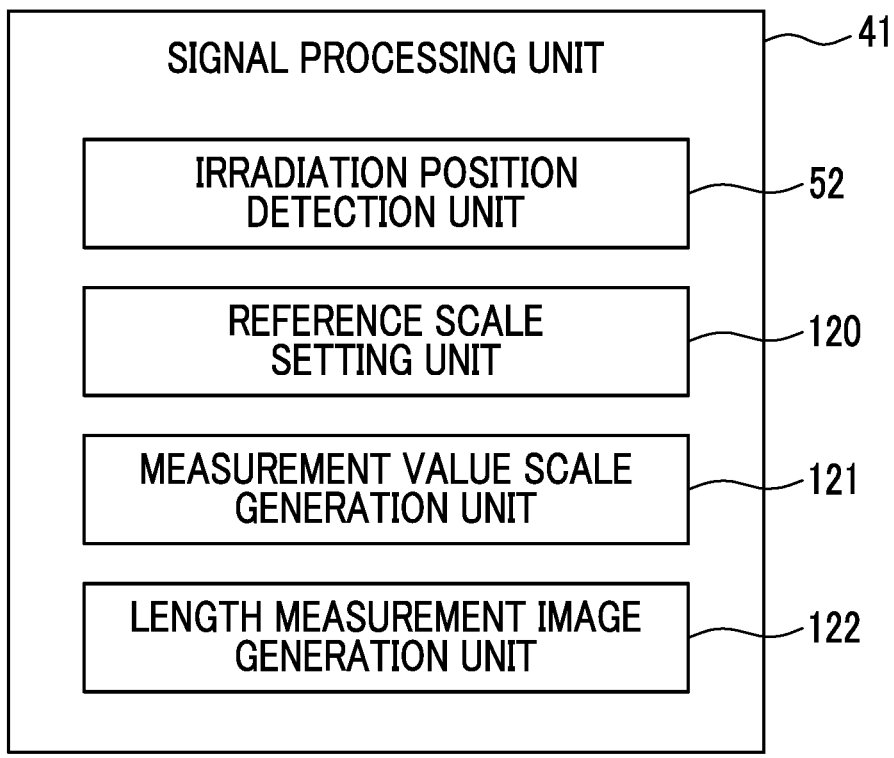
FIG. 26 is a block diagram showing functions of the signal processing unit used in a case where the shape of the virtual scale is changed in accordance with a measurement portion in a region-of-interest.

In addition, in the above embodiment, the shape of the virtual scale may be changed in accordance with a measurement portion of a region-of-interest. In this case, as shown in FIG. 26, the signal processing unit 45 of the extended processor device 17 comprises an irradiation position specifying unit 52, a reference scale setting unit 120, a measurement value scale generation unit 121, and a length measurement image generation unit 122. The reference scale setting unit 120 sets a reference scale showing the actual size of the subject on the basis of the position of the spot SP. The measurement value scale generation unit 121 generates a measurement value scale showing a measurement value measured at the measurement portion of the region-of-interest on the basis of the set reference scale. In addition, since the reference scale and the measurement value scale are virtual scales to be displayed on the captured image, the reference scale and the measurement value scale correspond to the virtual scale.

The region-of-interest is a region to which the user included in the subject should pay attention. The region-of-interest is, for example, a polyp or the like, having a higher possibility that the measurement is required. Additionally, the measurement portion is a portion for measuring the length or the like in the region-of-interest. For example, in a case where the region-of-interest is a reddish portion, the measurement portion is the longest portion of the reddish portion, or the like, and in a case where the region-of-interest is circular, the measurement portion is a diameter portion or the like of the region-of-interest.

The length measurement image generation unit 122 creates the length measurement image in which the measurement value scale is superimposed on the captured image. The measurement value scale is superimposed on the captured image in a state where the measurement value scale matches the measurement portion of the region-of-interest. The length measurement image is displayed on the extended display 18.

Figure 27:
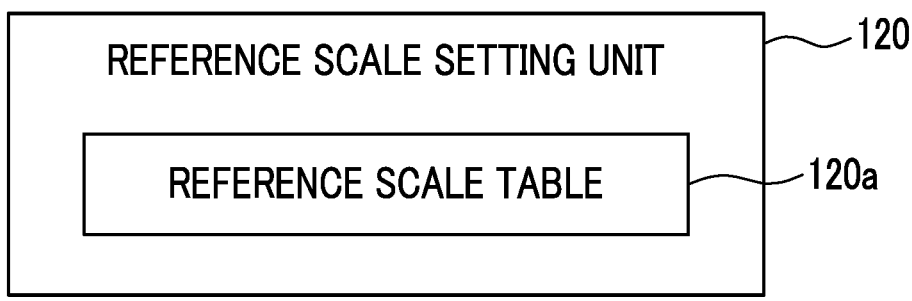
FIG. 27 is a block diagram showing functions of a reference scale setting unit.
Figure 28:
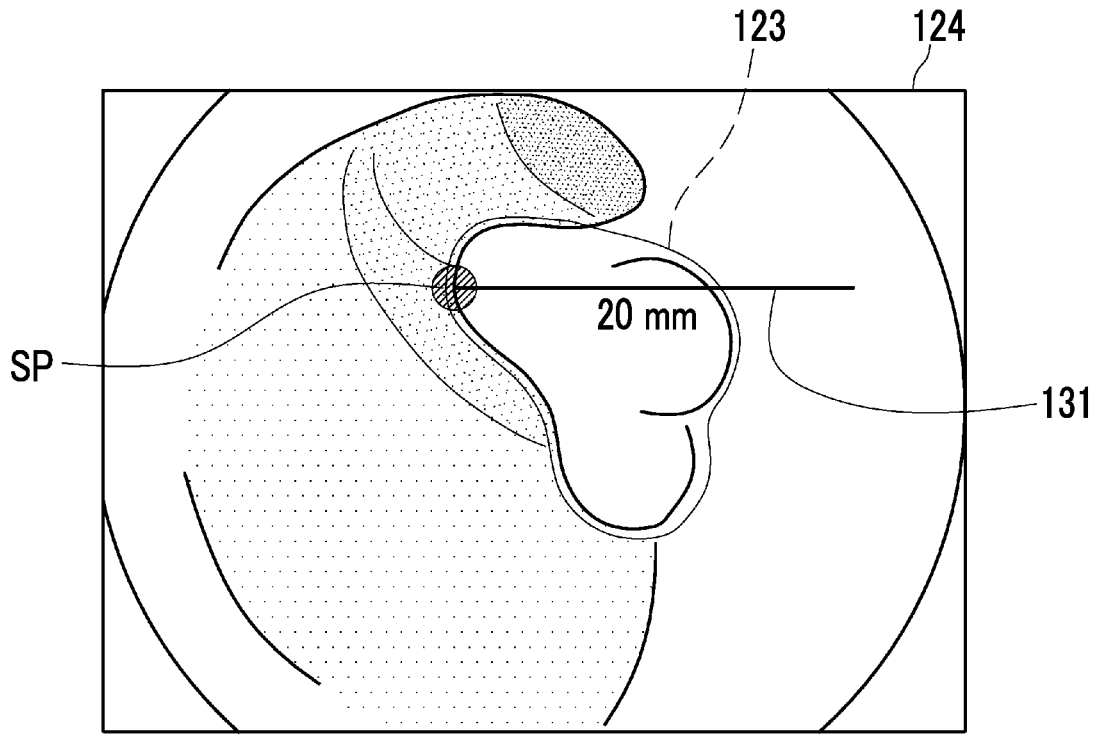
FIG. 28 is an image diagram showing the virtual scale superimposed and displayed on a polyp.

As shown in FIG. 27, the reference scale setting unit 120 includes a reference scale table 120a. The reference scale table 120a is correspondence information in which the position of the spot SP and the length measurement information corresponding to the actual size of the subject are associated with each other. In the length measurement mode, the captured image 114 in which the subject including the polyp 123, which is the object to be observed, is captured is input to the signal processing unit 45. As shown in FIG. 28, in the captured image 124, the polyp 123 has, for example, a three-dimensional shape in which spheres overlap each other. For example, the spot SP is formed at an end part on the polyp 123. The irradiation position detection unit 52 specifies the position of the spot SP on the basis of the captured image 124. The reference scale setting unit 120 sets a reference scale 131 showing the actual size of the subject corresponding to the position of the specified spot SP with reference to the reference scale table 120*a*.

The reference scale 131 is, for example, a line segment having a number of pixels corresponding to 20 mm in the actual size, and a numerical value and a unit showing the actual size. The reference scale 131 is not normally displayed on the extended display 18, but in a case where the reference scale 131 is displayed on the extended display 18, the reference scale is displayed as in the captured image 124.

Figure 29:
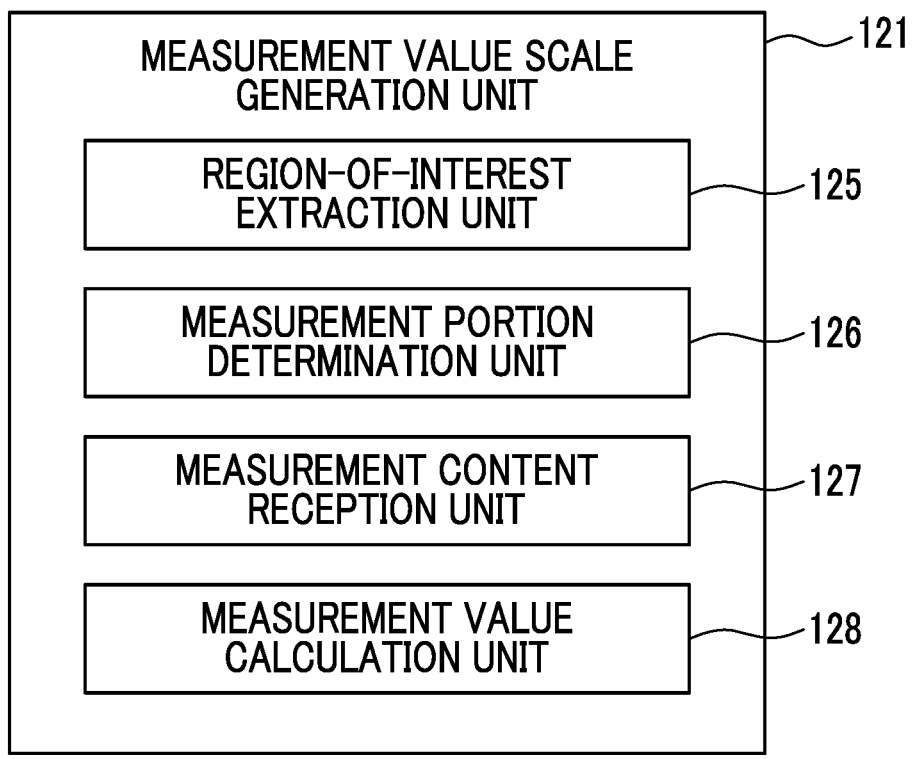
FIG. 29 is a block diagram showing functions of a measurement value scale generation unit.
Figure 30:
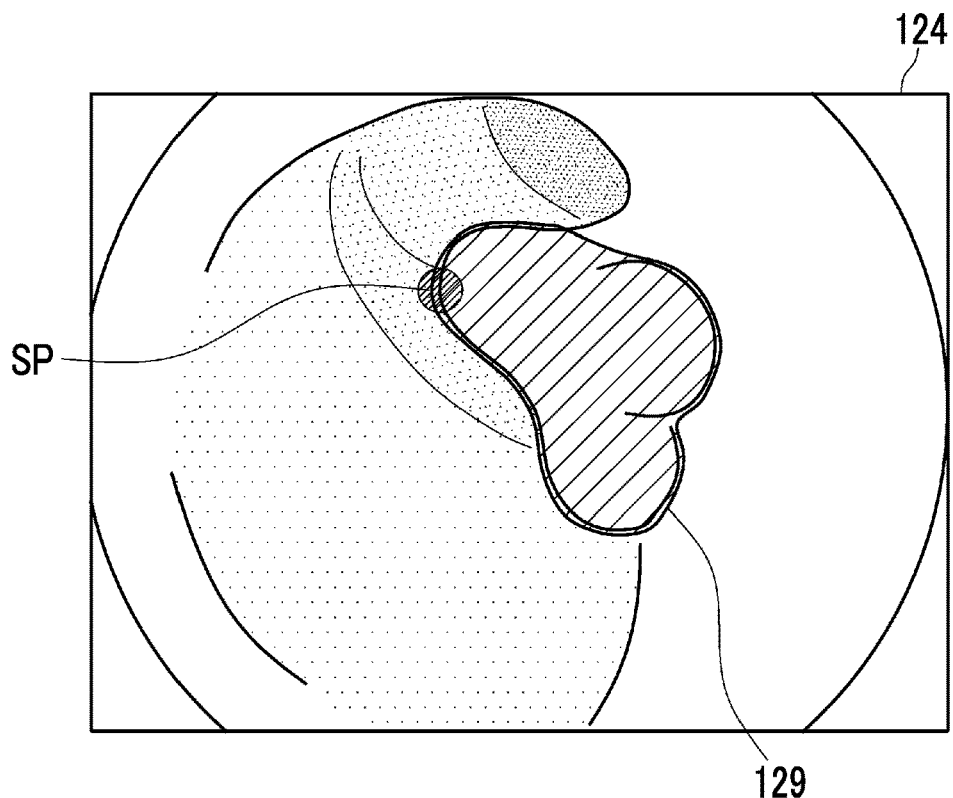
FIG. 30 is an image diagram showing the region-of-interest.
Figure 31:
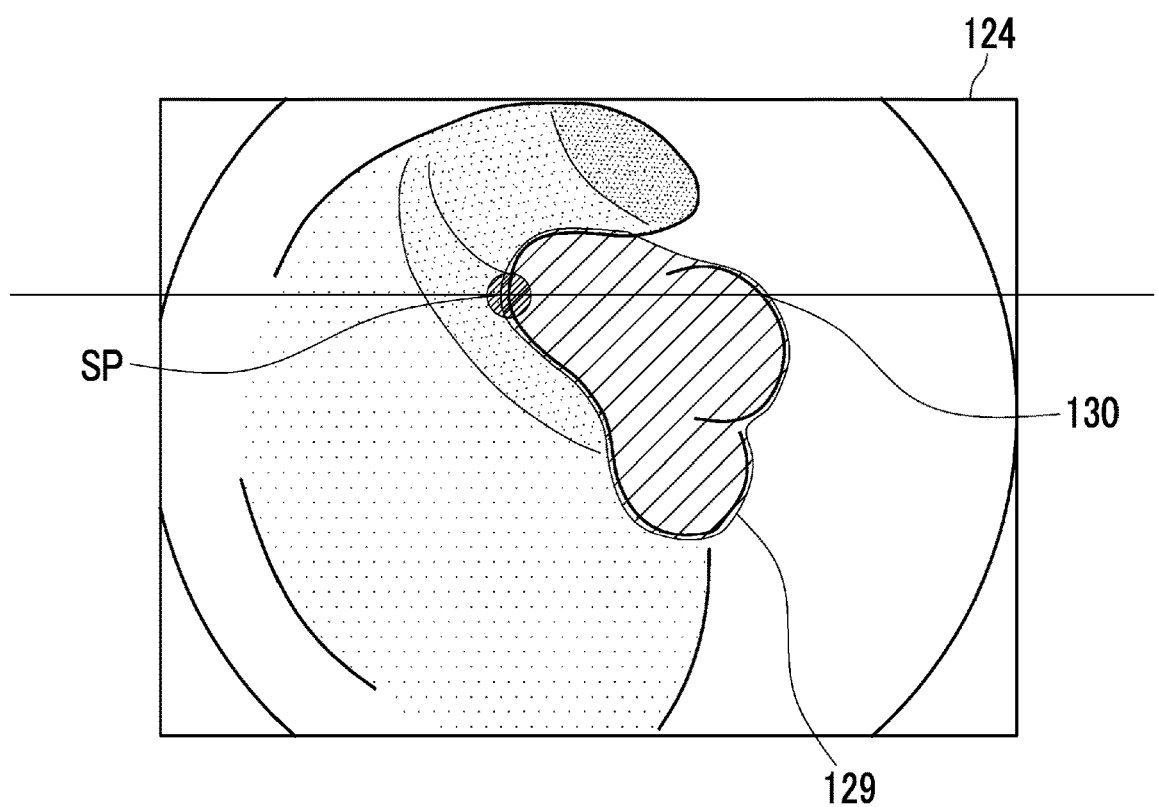
FIG. 31 is an explanatory diagram showing the measurement portion.

As shown in FIG. 29, the measurement value scale generation unit 121 comprises a region-of-interest extraction unit 125, a measurement portion determination unit 126, a measurement content reception unit 127, and a measurement value calculation unit 128. As shown in FIG. 30, the region-of-interest extraction unit 125 extracts a hatched region as the region-of-interest 129 as in the captured image 124. Next, as shown in FIG. 31, the measurement portion determination unit 126 extracts a horizontal edge position 130 with the spot SP as a base point as in the captured image 124, for example, in a case where a preset reference is a reference for measuring the portion of the region-of-interest in the horizontal direction with the spot SP as the base point. The measurement portion is between the spot SP and the horizontal edge position 130.

The measurement value calculation unit 128 generates a measurement value scale 132 so as to satisfy the following Equation (K1), for example, in a case where the actual size of the reference scale is set to L0, the number of pixels of the reference scale 131 on the captured image 124 is set to Aa, the number of pixels of the measurement portion in a case where the reference scale 131 is superimposed on the region-of-interest 129 in the captured image 124 is set to Ba, and the actual size of the measurement value scale 132 is set to L1.

$$L1 = L0 \times Ba/Aa \qquad \text{Equation (K1)}$$

Figure 32:
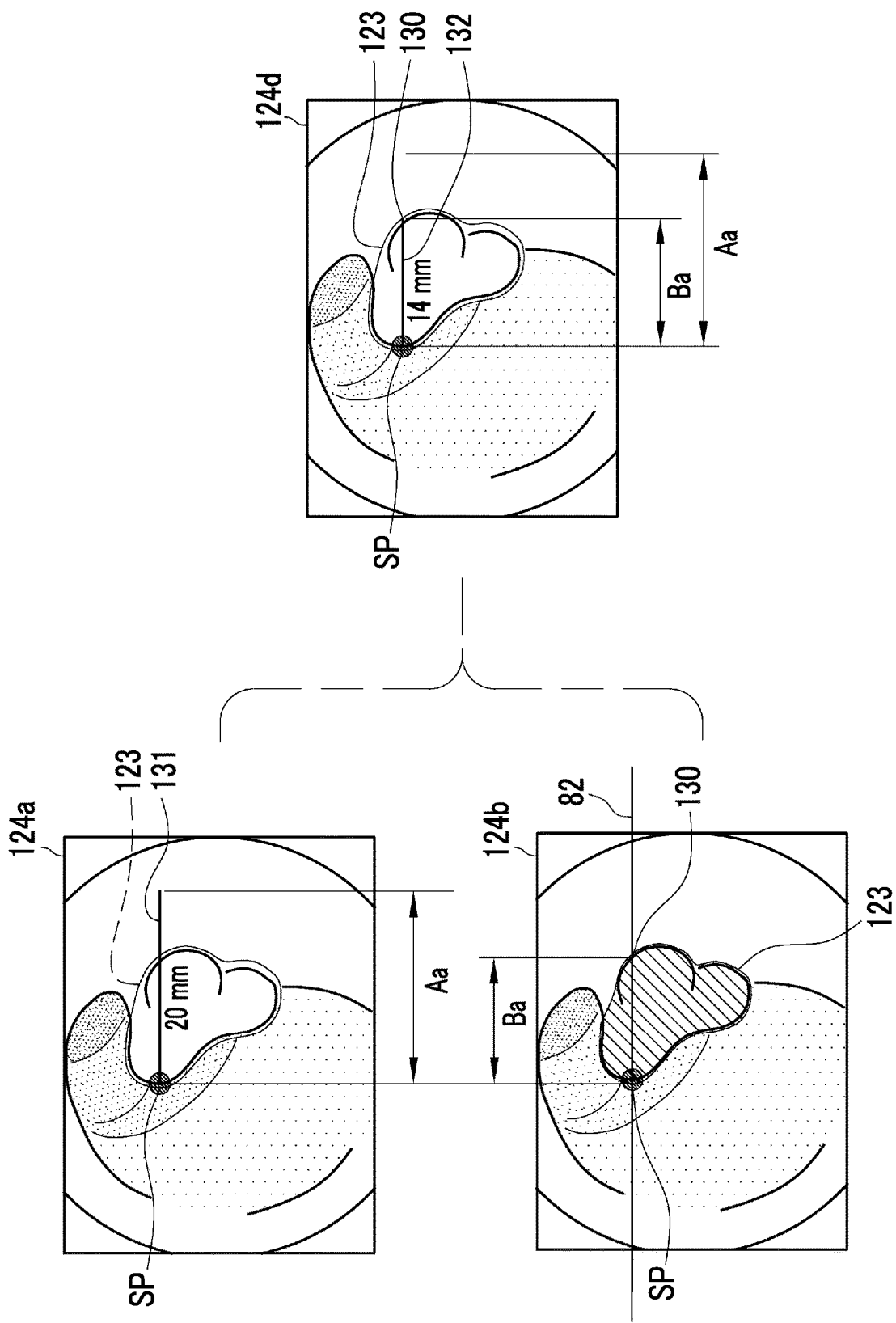
FIG. 32 is an image diagram regarding measurement value scales.

As shown in FIG. 32, the measurement value calculation unit 128 calculates the actual size of the measurement value scale 132 as 14 mm as in the captured image 124*d*, for example, in a case where Ba/Aa is 0.7 depending on the number of pixels Aa corresponding to the reference scale 131 shown in the captured image 124*a* and the number of pixels Bb corresponding to the measurement portion between the spot SP and the horizontal edge position 130 shown in the captured image 124*b* and in a case where the actual size of the reference scale 131 is 20 mm.

Figure 33:
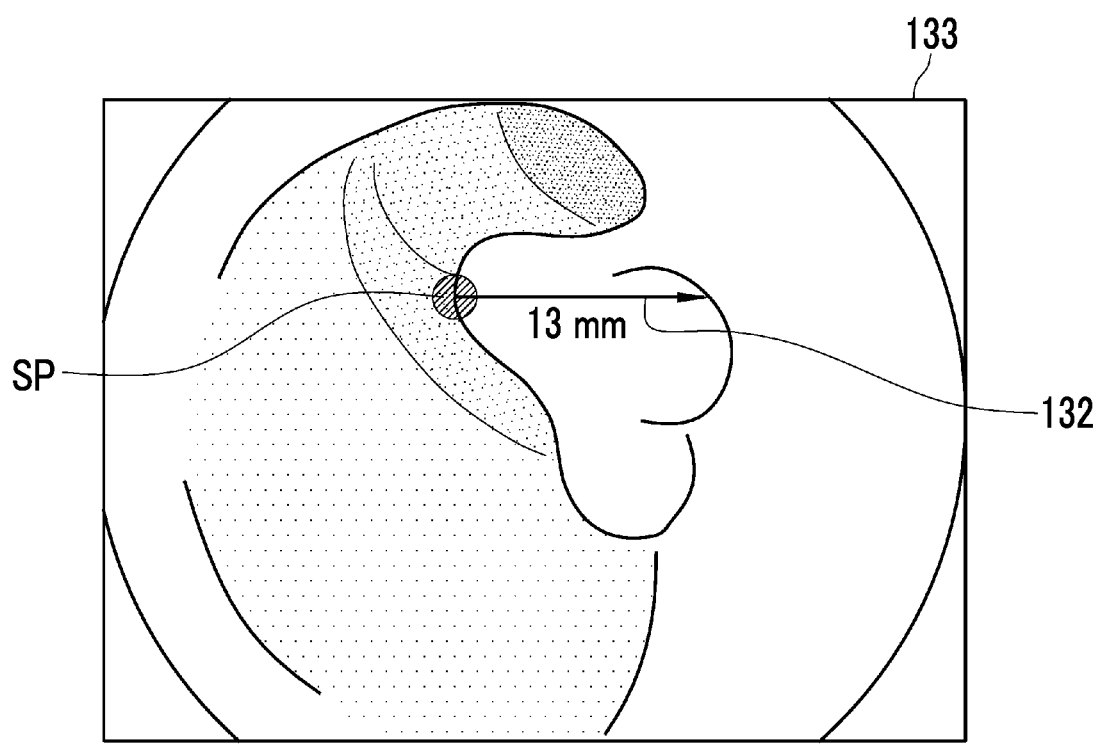
FIG. 33 is an image diagram showing the measurement value scales superimposed and displayed on the polyp.

The length measurement image generation unit 122 generates a length measurement image 133 in which the measurement value scale 132 is superimposed on the captured image 124. For example, as shown in FIG. 33, the measurement value scale 132 is superimposed on the captured image 124 by a figure such as an arrow that is the shape of a straight segment. The length measurement image 133 may include a numerical value of the actual size of the measurement value scale 132. In addition, the numerical value of the actual size of the measurement value scale 132 may be superimposed on the captured image 124 in a state where the measurement value scale is separated from a figure such as an arrow.

The type of the measurement value scale 132 can be selected from a plurality of types. The measurement content reception unit 127 receives the setting of the content of the measurement value scale and sends the content to the measurement value scale generation unit 121, and the length measurement image generation unit 122 generates the length measurement image 133 by using the measurement value scale 132 that the measurement value scale generation unit 121 has generated on the basis of the content.

In addition, it is preferable that the region-of-interest extraction unit 125 extracts the region-of-interest by using the learned model learned from the captured images acquired in the past. As models used for the learned model, various suitable can be used for image recognition by the machine learning. Models using a neural network can be preferably used for the purpose of recognizing a region-of-interest on an image. In a case where learning is performed on these models, the learning is performed using a captured image having information on the region-of-interest as teacher data. The information on the region-of-interest includes the presence or absence of the region-of-interest, the position or range of the region-of-interest, and the like. In addition, depending on models, the learning may be performed using a captured image having no information on the region-of-interest.

Additionally, it is preferable that the measurement portion determination unit 126 also determines the measurement portion by using the learned model learned from the captured images acquired in the past. Models or the like used for the learned model are the same as those of the region-of-interest extraction unit, but in a case where learning is performed on these models, the learning is performed using a captured image having information on the measurement portion. The information on the measurement portion includes a measurement value and a measurement portion therefor. In addition, depending on models, the learning may be performed using a captured image having no information on the measurement portion. In addition, the learned model used by the region-of-interest extraction unit 125 and the learned model used by the measurement portion determination unit 126 may be common to each other. In the case of the purpose of extracting the measurement portion, one learned model may be used to extract the measurement portion without excising the region-of-interest from the captured image 124.

Figure 34:
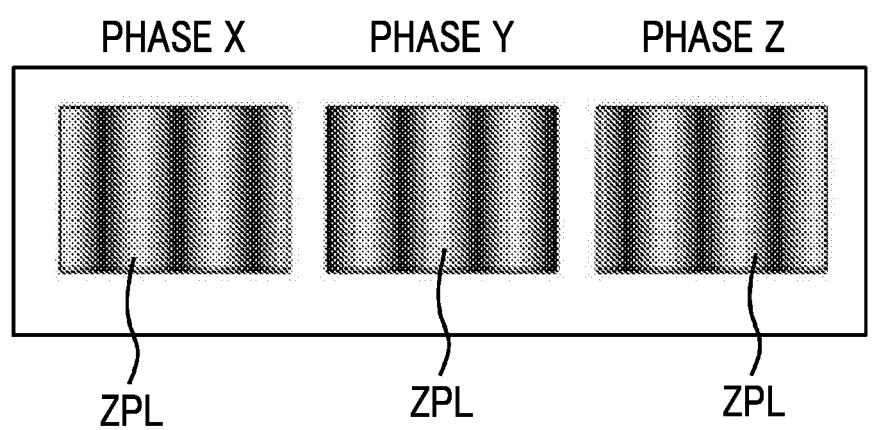
FIG. 34 is an explanatory diagram showing a striped pattern light ZPL.

In addition, as for the measurement light, as shown in FIG. 34, a striped pattern light ZPL formed as the light of a striped pattern on the subject in a case where the subject is irradiated may be used (for example, refer to JP2016-198304A). The striped pattern light ZPL is obtained by irradiating a liquid crystal shutter having variable transmittance (not shown) with a specific laser light and is formed from two different vertically striped patterns in which a region (transmissive region) through which the specific laser light is transmitted by the liquid crystal shutter and a region (non-transmissive region) through which the specific laser light is not transmitted are periodically repeated in the horizontal direction. In a case where the striped pattern light is used as the measurement light, the cycle of the striped pattern light varies depending on the distance from the subject. Therefore, the liquid crystal shutter shifts the cycle or phase of the striped pattern light and performs irradiation multiple times, and the three-dimensional shape of the subject is measured on the basis of a plurality of images obtained by shifting the period or phase.

Figure 35:
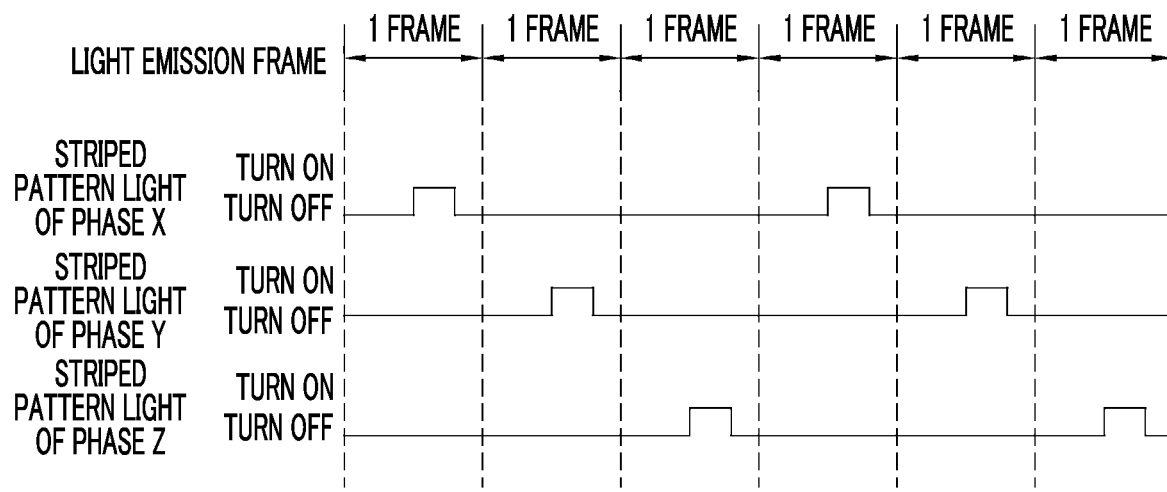
FIG. 35 is an explanatory diagram showing a light emission pattern of the striped pattern light ZPL having phases X, Y, and Z.

For example, the subject is alternately irradiated with a striped pattern light of a phase X, a striped pattern light of a phase Y, and a striped pattern light of phase Z. The striped pattern lights having phases X, Y, and Z are phase-shifted by 120° (2π/3) from the vertically striped pattern. In this case, a three-dimensional shape of the subject is measured using three types of images obtained on the basis of the respective striped pattern lights. For example, as shown in FIG. 35, it is preferable that the striped pattern light of the phase X, the striped pattern light of the phase Y, and the striped pattern light of the phase Z are switched in units of one frame (or several frames), respectively to irradiate the subject. In addition, it is preferable that the illumination light always irradiates the subject.

Figure 36:
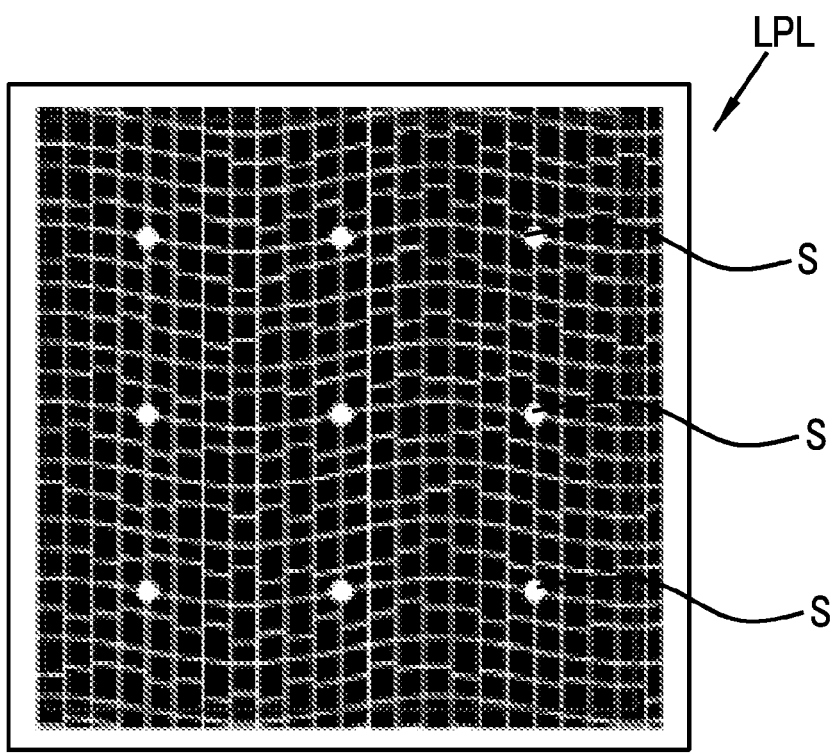
FIG. 36 is an explanatory diagram showing a measurement light LPL of a lattice-like pattern.

In addition, as for the measurement light, as shown in FIG. 36, the measurement light LPL having a lattice-like pattern formed as a lattice-like pattern in a case where the subject is irradiated may be used (for example, refer to JP2017-217215A). In this case, since the three-dimensional shape of the subject is measured depending on the deformation state of the lattice-like pattern in a case where the subject is irradiated with the measurement light LPL of the lattice-like pattern, it is required to accurately detect the lattice-like pattern. For that reason, the measurement light LPL of the lattice-like pattern is not a perfect lattice form but is slightly deformed from the lattice form, such as by being formed in a wavy manner so as to enhance the detection accuracy of the lattice-like pattern. Additionally, the lattice-like pattern is provided with an S code showing that the end points of the left and right horizontal lines are continuous. In a case where the lattice-like pattern is detected, not only the pattern but also the S code is detected to enhance the detection accuracy of the pattern. In addition, the lattice-like pattern may be a pattern in which a plurality of spots are arranged vertically and horizontally in a lattice form in addition to a pattern in which vertical lines and horizontal lines are regularly arranged.

Figure 37:
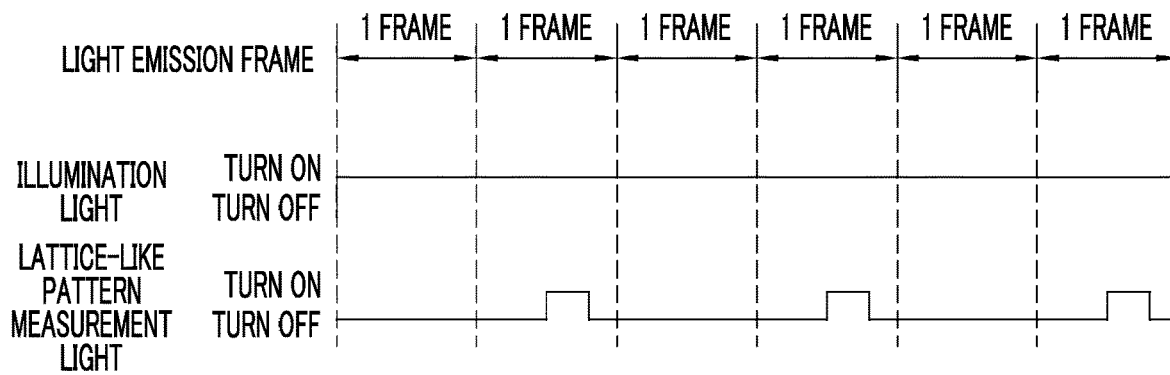
FIG. 37 is an explanatory diagram showing a light emission pattern in which the measurement light of the lattice-like pattern is intermittently emitted.

In a case where the measurement light LPL having a lattice-like pattern is used as the measurement light, the subject may be always irradiated with the illumination light and the measurement light LPL having a lattice-like pattern during the length measurement mode. Additionally, as shown in FIG. 37, while the illumination light always illuminates the subject, the lattice-like pattern measurement light LPL is repeatedly turned on and off (or dimmed) every frame (or every several frames) to intermittently irradiate the subject with the lattice-like pattern measurement light LPL. In this case, in a frame in which the measurement light LPL of the lattice-like pattern is turned on, a three-dimensional shape based on the measurement light LPL of the lattice-like pattern is measured. Then, it is preferable to superimpose and display the measurement result of the three-dimensional shape on the image obtained in a frame in which irradiation with only the illumination light is performed.

Figure 38:
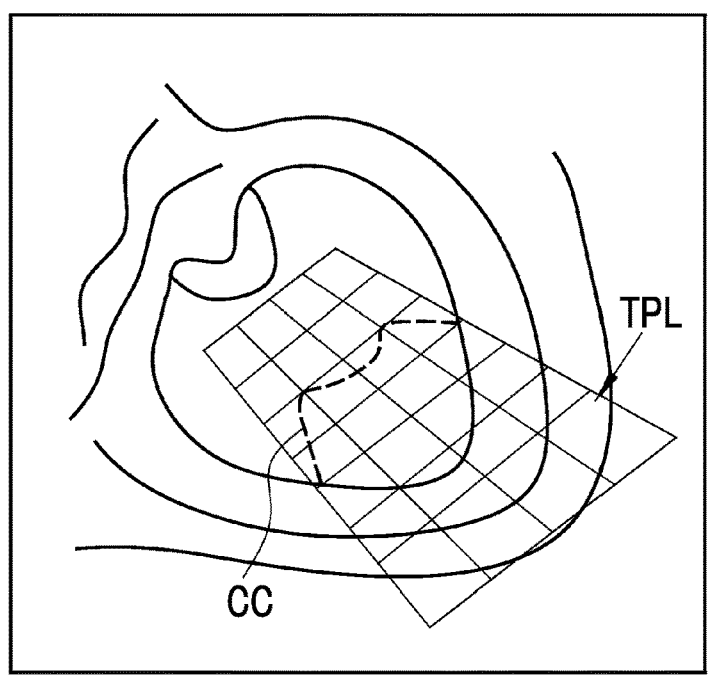
FIG. 38 is an explanatory diagram showing a three-dimensional planar light TPL.

In addition, as for the measurement light, as shown in FIG. 38, a three-dimensional planar light TPL represented by mesh lines on the subject image may be used (for example, refer to JP2017-508529A, corresponding to US 2016/0287141A1). In this case, the distal end part 12d is moved such that the three-dimensional planar light TPL matches the measurement target. Then, in a case where the three-dimensional planar light TPL intersects the measurement target, the distance of an intersection curve CC between the three-dimensional planar light TPL and the subject is calculated by the processing based on a manual operation such as a user interface or automatic processing.

Figure 39:
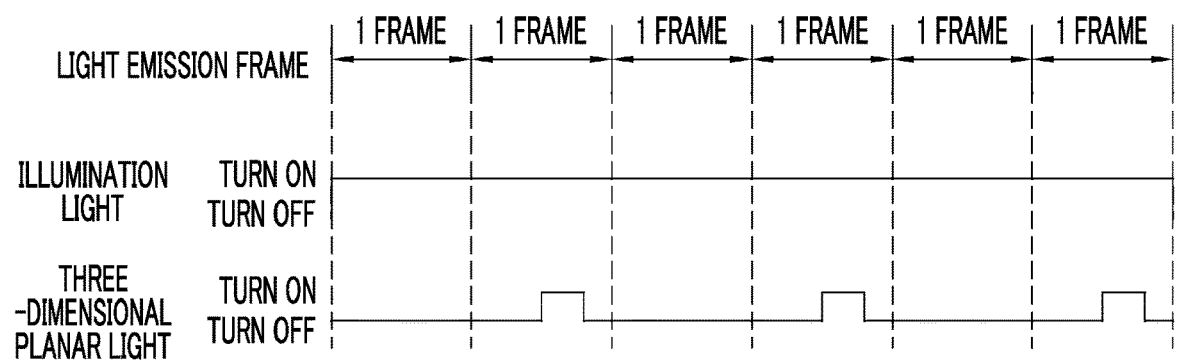
FIG. 39 is an explanatory diagram showing a light emission pattern in which the three-dimensional planar light TPL is intermittently emitted.

In a case where the three-dimensional planar light TPL is used as the measurement light, the subject may be always irradiated with the illumination light and the three-dimensional planar light TPL during the length measurement mode. Additionally, as shown in FIG. 39, while the illumination light always illuminates the subject, the three-dimensional planar light TPL is repeatedly turned on and off (or dimmed) every frame (or every several frames) to intermittently irradiate the subject with the lattice-like pattern measurement light LPL.

In the above embodiment, the hardware structure of a processing unit that executes various kinds of processing such as the first signal processing unit 50, the second signal processing unit 51, the still image automatic acquisition unit 66, the image reception unit 101, the still image combination unit 102, the still image discrimination unit 105, the examination purpose recognition unit 106, and the display control unit 107 is various processors as shown below. The various processors include a central processing unit (CPU) that is a general-purpose processor that executes software (programs) to function as various processing units, a programmable logic device (PLD), which is a processor capable of changing the circuit configuration after manufacturing, such as a field programmable gate array (FPGA), a dedicated electric circuit that is a processor having a circuit configuration designed in a dedicated manner to execute various processing, and the like.

One processing unit may be constituted of one of the various processors, or may be constituted of a combination (for example, a plurality of FPGAs or a combination of a CPU and an FPGA) of two or more processors of the same type or different types. Additionally, a plurality of processing units may be constituted of one processor. As an example in which the plurality of processing units is constituted of one processor, firstly, as represented by a computer such as a client or a server, there is a form in which one processor is configured by a combination of one or more CPUs and software and this processor functions as the plurality of processing units. Secondly, as represented by system on chip (SoC), there is a form in which a processor that realizes the functions of the entire system including a plurality of processing units with one integrated circuit ((IC) chip is used. In this way, the various processing units are configured using one or more of the various processors as the hardware structure.

Moreover, the hardware structure of the various processors is, more specifically, an electric circuit (circuitry) in a form in which circuit elements such as semiconductor elements are combined together. Additionally, the hardware structure of the storage unit is a storage device such as a hard disk drive (HDD) or solid state drive (SSD).

EXPLANATION OF REFERENCES

5: endoscopy service support system
10: endoscope system
12: endoscope
12a: insertion part
12b: operating part
12c: bendable part
12d: distal end part
12f: mode selection switch
12g: still image acquisition instruction switch
12h: zoom operation part
13: light source device
14: processor device
15: display
16: user interface
17: extended processor device
18: extended display
20: light source unit
21: light source processor
22: Illumination optical system
22a: Illumination lens 23: measurement light emitting unit
24: imaging optical system
24a: objective lens
24b: zoom lens
25: imaging element
26: CDS/AGC circuit
27: A/D converter
28, 30: communication I/F
29: imaging control unit
32: system control unit
33: reception unit
34: signal processing unit
35: display control unit
36: data transmission/reception unit
37: still image saving unit
40: data transmission/reception unit
41: signal processing unit
42: display control unit
50: first signal processing unit
51: second signal processing unit
52: irradiation position detection unit
53: scale table
54: zoom function recognition unit
55: second virtual scale setting unit
57: intersection line
58: graduations
60, 62, 64: second virtual scale
60a to 60f: circular scale
62a: vertical axis
62b: horizontal axis
62c: intersection point
66: still image automatic acquisition unit
70: removed specimen
100: endoscopy service support device
101: image reception unit
102: still image combination unit
105: still image discrimination unit
106: examination purpose recognition unit
107: display control unit
108: service support display
109: user interface
110: image memory storage
110a: case image folder
112: internal still image
113: external still image
114, 115: length measurement information display region
116: examination purpose selection screen
116a: observation selection icon
116b: treatment selection icon
120: reference scale setting unit
120a: reference scale table
121: measurement value scale generation unit
122: length measurement image generation unit
123: polyp
124, 124a, 124b, 124d: captured image
125: region-of-interest detection unit
126: measurement portion determination unit
127: measurement content reception unit
128: measurement value calculation unit
129: region-of-interest
130: horizontal edge position
131: reference scale
132: measurement value scale
133: length measurement image
CC: intersection curve
CTx, Cty: center
FLx: illumination light single emission frame
FLy: measurement light emission frame
LG: light guide
Lm: measurement light
LPL: lattice-like pattern light
M1, M2, M3: first virtual scale
M41, M42, M43: virtual scale
M4A, M4B, M4C: first virtual scale
M5A, M5B, M5C: first virtual scale
M6A, M6B, M6C: first virtual scale
NT: network
P: polyp
PT: patient
Px: near end
Py: center vicinity
Pz: far end
SP: spot
SP1, SP2, SP3, SP4, SP5: spot
TPL 3D: three-dimensional planar light
X1: external still image
Y1, Y2, Y3, YN: internal still image
ZPL: striped pattern light

What is claimed is:

1. An endoscopy service support device comprising:
a processor for service support, configured to:
receive a still image acquired by an endoscope system;
discriminate whether the still image is an internal still image or an external still image on the basis of a feature quantity of the still image;
perform still image collation processing for collating the internal still image with the external still image out of the still images and combine the internal still image with the external still image on the basis of at least a result of the still image collation processing; and
display the combined internal still image and external still image on a service support display, wherein
the internal still image is internal to a body, and
the external still image is external to the body.

2. The endoscopy service support device according to claim 1,
wherein the internal still image or the external still image is associated with an examination purpose including treatment or observation, and
the processor for service support is configured to combine the external still image with an internal still image of which the examination purpose is the treatment, out of the internal still images that match the external still image as a result of the still image collation processing.

3. The endoscopy service support device according to claim 2,
wherein the processor for service support is configured to recognize the examination purpose on the basis of a feature amount of the internal still image.

4. The endoscopy service support device according to claim 1,
wherein length measurement information is associated with the internal still image or the external still image, and
the processor for service support is configured to combine the external still image with an internal still image of which the length measurement information matches that of the external still image, out of the internal still images that match the external still image, as a result of the still image collation processing.

5. The endoscopy service support device according to claim 4, wherein the length measurement information is size information in which a length measurement object is quantified on the basis of a virtual scale.

6. The endoscopy service support device according to claim 1,
wherein the service support display is provided with a length measurement information display region for displaying length measurement information of at least one of the internal still image or the external still image, and an examination purpose selection screen for selecting an examination purpose.

7. An endoscopy service support system comprising:
an endoscope system having an endoscope that acquires a still image manually or automatically obtained by imaging a subject by using an imaging optical system; and
the endoscopy service support device according to claim 1,
wherein the internal still image or the external still image is obtained by the endoscope.

8. The endoscopy service support system according to claim 7,
wherein the endoscope has a measurement light emitting unit that emits a measurement light in a state where an optical axis of the measurement light and an optical axis of the imaging optical system intersect each other, and acquires the still image by imaging the subject illuminated with the measurement light by using the imaging optical system, and
the endoscope system further comprises:
a processor device that acquires length measurement information on the basis of an irradiation position of the measurement light included in the still image.

9. The endoscopy service support system according to claim 8,
wherein the length measurement information is information based on a virtual scale for measuring a size of the subject,
the processor device includes an endoscope processor, and
the endoscope processor is configured to:
detect an irradiation position of the measurement light from the still image; and
set a first virtual scale in which a scale display position varies in accordance with the irradiation position of the measurement light as the virtual scale by referring to a scale table in which a virtual scale image of which a display mode varies depending on the irradiation position of the measurement light and the scale display position and the irradiation position of the measurement light are stored in association with each other.

10. The endoscopy service support system according to claim 8,
wherein the length measurement information is information based on a virtual scale for measuring a size of the subject,
the endoscope has a zoom function,
the processor device includes an endoscope processor, and
the endoscope processor is configured to:
set a second virtual scale of which a scale display position is fixed as the virtual scale in a case where the zoom function is ON and has a magnification ratio equal to or more than a specific magnification ratio.

11. The endoscopy service support system according to claim 10,
wherein the second virtual scale has the same display mode regardless of a position of a screen, or has a display mode that varies depending on the position of the screen.

12. A method of operating an endoscopy service support device, the method being executed by a processor for service support and comprising:
a step of receiving a still image acquired by an endoscope system;
a step of discriminating whether the still image is an internal still image or an external still image on the basis of a feature quantity of the still image;
a step of performing still image collation processing for collating the internal still image with the external still image out of the still images and combining the internal still image with the external still image on the basis of at least a result of the still image collation processing; and
a step of displaying the combined internal still image and external still image on a service support display, wherein
the internal still image is internal to a body, and
the external still image is external to the body.

* * * * *